United States Patent [19]

Jayasena et al.

[11] Patent Number: 5,734,034
[45] Date of Patent: Mar. 31, 1998

[54] NUCLEIC ACID LIGAND INHIBITORS OF HUMAN NEUTROPHIL ELASTASE

[75] Inventors: Sumedha D. Jayasena; Larry Gold, both of Boulder, Colo.

[73] Assignee: NeXstar Pharmaceuticals, Inc., Boulder, Colo.

[21] Appl. No.: 441,828

[22] Filed: May 16, 1995

Related U.S. Application Data

[60] Division of Ser. No. 199,507, Feb. 22, 1994, Pat. No. 5,472,841, which is a continuation-in-part of Ser. No. 714, 131, Jun. 10, 1991, Pat. No. 5,475,096, and Ser. No. 964, 624, Oct. 21, 1992, Pat. No. 5,496,938, said Ser. No. 714,131, is a continuation-in-part of Ser. No. 536,428, Jun. 11, 1990, abandoned.

[51] Int. Cl.$^6$ .................. C07H 21/02; C07H 21/04; C12P 19/34; C12Q 1/68
[52] U.S. Cl. .................. 536/23.1; 536/25.4; 435/6; 435/91.2; 435/218; 935/77; 935/78
[58] Field of Search .................. 536/23.1, 25.4; 435/6, 92.1; 935/77, 78; 438/218

[56] References Cited

U.S. PATENT DOCUMENTS 5,270,163  12/1993  Gold et al. .................. 435/6

FOREIGN PATENT DOCUMENTS 2 183 661  6/1987  United Kingdom .
WO 89/06694  7/1989  WIPO .
WO 91/19813  12/1991  WIPO .

OTHER PUBLICATIONS

Hobbs et al., Biochemistry 12 (25): 5138–5145 (1973).
Lestienne, et al. Biochimie 65: 49–52 (1983).
Oleksyszyn and Powers (1991) Biochemistry 30:485.
Oleksyszyn and Powers (1989) Biochemical and Biophysical Research Communications 161:143.
Simon et al. (1988) Adv. Exp. Med. Biol. 240:65.
Simon et al. (1988) Exp. Lung Res. 14:85.
Vered et al. (1988) Exp. Lung Res. 14:67.
Joyce (1989) Gene 82:83.
Joyce and Inoue (1989) Nucleic Acids Research 17:711.
Ellington and Szostak (1990) Abstract of papers presented at the 1990 meeting on RNA Processing, Cold Spring Harbor Laboratory, Cold Spring Harbor, NY, p. 226.
Kramer et al. (1974) J. Mol. Biol. 89:719.
Levisohn and Spiegelman (1969) Proc. Natl. Acad. Sci. USA 63:805.
Levisohn and Spiegelman (1968) Proc. Natl. Acad. Sci. USA 60:866.
Oliphant et al. (1989) Mol. Cell. Biol. 9:2944.
Oliphant and Struhl (1988) Nucleic Acids Research 16:7673.
Oliphant and Struhl (1987) Methods in Enzymology 155:568.
Oliphant et al. (1986) Gene 44:177.
Robertson and Joyce (1990) Nature 344:467.
Thiesen and Bach (1990) Nucleic Acids Research 18:203.
Awang and Sen (1993) Biochemistry 32:11453.
Barrett (1978) Agents and Actions 8:11.
Bonney et al. (1989) J. Cell. Biochem. 39:47.
Dewald et al. (1975) J. Exp. Med. 141:709.
Doherty et al. (1986) Nature 322:192.
Gadek et al. (1981) J. Clin. Invest. 68:1158.
Garver et al. (1986) New Engl. J. Med. 314:762.
Gast et al. (1990) Am. Rev. Respir. Dis. 141:889.
Gauthier et al. (1982) Biochim. Biophys. Acta. 700:178.
Hemmi et al. (1985) Biochemistry 24:1841.
Janus et al. (1985) The Lancet *i*:152.
Kang et al. (1992) Nature 356:126.
Kaplan et al. (1973) J. Lab Clin. Med. 82:349.
Kennedy et al. (1987) Eur. J. Resir. Dis. 71:472.
Kinzler et al. (1989) Nucleic Acids Research 17:3645.
Knight et al. (1992) Biochemistry 31:4980.
Lestienne et al. (1983) Biochemie 65:49.
Navia et al. (1989) Proc. Natl. Acad. Sci. USA 86:7.
Powers et al. (1977) Biochim. Biophys. Acta. 485:156.
Sanders and Moore (1983) Amer. Rev. Respir. Dis. 127:554.
Sen et al. (1988) Nature 334:364.
Sinha et al. (1987) Proc. Natl. Acad. Sci. USA 84:2228.
Snider et al. 91985) Am. Rev. Respir. Dis. 132:1155.
Stein et al. (1993) Science 261:1004.
Stone et al. (1990) Am. Rev. Respir. Dis. 141:47.
Sundquist et al. (1993) Proc. Natl. Acad. Sci. USA 90:3393.
Sundquist et al. (1989) Nature 342:825.
Thompson and Ohlsson (1986) Proc. Natl. Acad. Sci. 83:6692.
Tuerk and Gold (1990) Science 249:505.
Tuerk et al. (1992) Proc. Natl. Acad. Sci. USA 89:6988.
Weiland et al. (1986) Am. Rev. Respir. Dis. 133:218.
Wiedow et al. (1990) J. Biol. Chem. 265:14791.
Williams et al. (1991) Am. Rev. Respir. Dis. 144:875.
Williamson et al. (1989) Cell 59:871.
Zimmerman et al. (1975) J. Mol. Biol. 92:181.
Zon (1988) Pharm. Res. 5:539.

*Primary Examiner*—Stephanie W. Zitomer
*Attorney, Agent, or Firm*—Swanson & Bratschun LLC

[57] ABSTRACT

Methods are described for the identification and preparation of nucleic acid ligands to human neutrophil elastase. Included in the invention are specific RNA and DNA ligands to elastase identified by the SELEX method.

12 Claims, 16 Drawing Sheets

```
         G
      G     G
   G           G
      G           U
         G    G
         G = C
         G = C
         U = A
         U = G
         C = G
         C = G
         G = U
         C     A
         A = U
         U = A
         A = U
         C = G
5'-GGUAGA     GUA-3'
```

SEQ ID NO: 7

FIG. 8A

SEQ ID NO: 7

Primer-Template Mixture I

Template

5'-GCCGGATCCCGGGGCCCTCATGTCGAA-[40]n-TTGAGGCGTTATTCTGAGCTCCC
    SEQ ID NO:54

Primers

5'-CCGAAGCTTAATACGACTCACTATAGGGAGCTCAGAATAAACGCTCAA   5G1
    SEQ ID NO:55

5'-GCCGGATCCCGGGGCCCTCATGTCGAA   3G1
    SEQ ID NO:56

Primer-Template Mixture II

Template:

5'-CCCCTGCAGGTGATTTGCTCAAGT-(40)n-AGTATCGCTAATCAGGCGGATC
    SEQ ID NO:57

Primers

5'-CCGAAGCTTAATACGACTCACTATAGGGATCCGCCTGATTAGCGATACT   5G2
    SEQ ID NO:58

5'-CCCCTGCAGGTGATTTGCTCAAGT   3G2
    SEQ ID NO:59

FIG. 12

SEQUENCE LISTING ( 1 ) GENERAL INFORMATION:

( i i i ) NUMBER OF SEQUENCES: 59

( 2 ) INFORMATION FOR SEQ ID NO:1:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

GAGUAGGCUU  GACGCCUGGG  GGGGUAUGGC  UUCGACUGCG    40

( 2 ) INFORMATION FOR SEQ ID NO:2:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

GAGUAGGCUU  GACGCCUGGG  GGGGUAUGGC  UUCAACUGCG    40

( 2 ) INFORMATION FOR SEQ ID NO:3:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

GAGUAGGCUU  GACGCUGGGG  GGGUAUGGCU  UCGACUUGCG    40

( 2 ) INFORMATION FOR SEQ ID NO:4:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:4:

```
AGAGGUAGGC UUGACGCCUG GGGGGGUAUG GCUCCGACUG CG                42
```

( 2 ) INFORMATION FOR SEQ ID NO:5:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:5:

```
GGUAGACAUA CGCCUUGGGG GGGUGUCAGG GUAUAUGGUA                   40
```

( 2 ) INFORMATION FOR SEQ ID NO:6:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:6:

```
GGCAGACAUA CGCCUUGGGG GGGUGUCAGG GUAUAUGGUA                   40
```

( 2 ) INFORMATION FOR SEQ ID NO:7:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:7:

```
GGUAGACAUA CGCCUUGGGG GGGUGCCAGG GUAUAUGGUA                   40
```

( 2 ) INFORMATION FOR SEQ ID NO:8:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:8:

```
GGUAGACAUA CGCCUUGGGG GGGUAUCAGG GUAUAUGGUA                   40
```

( 2 ) INFORMATION FOR SEQ ID NO:9:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:9:

```
GGCAGACAUA CGCCUUGGGG GGGUGUCAGG GUAUAUGGCA                   40
```

( 2 ) INFORMATION FOR SEQ ID NO:10:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:10:

```
GGCAGACAUA CGCCUUGGGG GGGUUUCAGG GUAUAUGGCA                   40
```

( 2 ) INFORMATION FOR SEQ ID NO:11:

( i ) SEQUENCE CHARACTERISTICS:
    ( A ) LENGTH: 40 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:11:

AGAAUGAAUG UGAUGAACAG GUGUCGGGGU GGAUGGGUGG    40

( 2 ) INFORMATION FOR SEQ ID NO:12:

( i ) SEQUENCE CHARACTERISTICS:
    ( A ) LENGTH: 40 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:12:

GGAAUGAAUG UGAUGAACAG GUGUCGGGGU GGAUGGGUGG    40

( 2 ) INFORMATION FOR SEQ ID NO:13:

( i ) SEQUENCE CHARACTERISTICS:
    ( A ) LENGTH: 39 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:13:

GAAUGAAUGU GAUGAACAGG UGUCGGGGUG GAUGGGUGG    39

( 2 ) INFORMATION FOR SEQ ID NO:14:

( i ) SEQUENCE CHARACTERISTICS:
    ( A ) LENGTH: 40 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:14:

CGCCUUAGUC GCCAUAAUGC UGUCGGGGUG GAUAGGGUGG    40

( 2 ) INFORMATION FOR SEQ ID NO:15:

( i ) SEQUENCE CHARACTERISTICS:
    ( A ) LENGTH: 40 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:15:

UGCCCGGCAG UACUGCACGG CCUCGGGGGG GACCAGGGAG    40

( 2 ) INFORMATION FOR SEQ ID NO:16:

( i ) SEQUENCE CHARACTERISTICS:
    ( A ) LENGTH: 40 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:16:

AUCGGAUAGC GCCGCGAUGG CGUCGGGGG GGACCAGGGA    40

( 2 ) INFORMATION FOR SEQ ID NO:17:

( i ) SEQUENCE CHARACTERISTICS:
          ( A ) LENGTH: 39 base pairs
          ( B ) TYPE: nucleic acid
          ( C ) STRANDEDNESS: single
          ( D ) TOPOLOGY: linear ( x i ) SEQUENCE DESCRIPTION: SEQ ID NO:17:

```
GUACUACUGC AAGCCCGUGU GGCGCGGUCA GUGGGUGGC                              39
```

( 2 ) INFORMATION FOR SEQ ID NO:18:

( i ) SEQUENCE CHARACTERISTICS:
          ( A ) LENGTH: 40 base pairs
          ( B ) TYPE: nucleic acid
          ( C ) STRANDEDNESS: single
          ( D ) TOPOLOGY: linear ( x i ) SEQUENCE DESCRIPTION: SEQ ID NO:18:

```
GUACUACUGC AAGCCCGUGU GGCGCGGUCA GUGGGUGGCC                             40
```

( 2 ) INFORMATION FOR SEQ ID NO:19:

( i ) SEQUENCE CHARACTERISTICS:
          ( A ) LENGTH: 40 base pairs
          ( B ) TYPE: nucleic acid
          ( C ) STRANDEDNESS: single
          ( D ) TOPOLOGY: linear ( x i ) SEQUENCE DESCRIPTION: SEQ ID NO:19:

```
CGGAUCGGGC GGUCGUCUAG CGGGAUGGCG UGCGGGUGGA                             40
```

( 2 ) INFORMATION FOR SEQ ID NO:20:

( i ) SEQUENCE CHARACTERISTICS:
          ( A ) LENGTH: 39 base pairs
          ( B ) TYPE: nucleic acid
          ( C ) STRANDEDNESS: single
          ( D ) TOPOLOGY: linear ( x i ) SEQUENCE DESCRIPTION: SEQ ID NO:20:

```
UGACCGGGUC GACAUGCCUG AGGUGUGGCC AGUGGGUGG                              39
```

( 2 ) INFORMATION FOR SEQ ID NO:21:

( i ) SEQUENCE CHARACTERISTICS:
          ( A ) LENGTH: 37 base pairs
          ( B ) TYPE: nucleic acid
          ( C ) STRANDEDNESS: single
          ( D ) TOPOLOGY: linear ( x i ) SEQUENCE DESCRIPTION: SEQ ID NO:21:

```
GGCCCUCUGA ACCGUCUGGG CGUGGUUAGU GGGUGGC                                37
```

( 2 ) INFORMATION FOR SEQ ID NO:22:

( i ) SEQUENCE CHARACTERISTICS:
          ( A ) LENGTH: 40 base pairs
          ( B ) TYPE: nucleic acid
          ( C ) STRANDEDNESS: single
          ( D ) TOPOLOGY: linear ( x i ) SEQUENCE DESCRIPTION: SEQ ID NO:22:

```
UGACCGGGCC GACAUGCUUG AGGUGUGGCC CAGUGGGUGG                             40
```

( 2 ) INFORMATION FOR SEQ ID NO:23:

( i ) SEQUENCE CHARACTERISTICS:
  ( A ) LENGTH: 40 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:23:

GACGCGUGCU GGCCUCGACC GUGUGGGUGC GGAUGGGUGG                    40

( 2 ) INFORMATION FOR SEQ ID NO:24:

( i ) SEQUENCE CHARACTERISTICS:
    ( A ) LENGTH: 44 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:24:

UGAGGUUGAG UAGUCGUGGU AAUGGCCACG GCUGGGGGGG UCGG               44

( 2 ) INFORMATION FOR SEQ ID NO:25:

( i ) SEQUENCE CHARACTERISTICS:
    ( A ) LENGTH: 40 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:25:

UGGAUAGCGC UGCGUGACCG CGCUGGGGGG GUUGGCAGGG                    40

( 2 ) INFORMATION FOR SEQ ID NO:26:

( i ) SEQUENCE CHARACTERISTICS:
    ( A ) LENGTH: 40 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:26:

ACCTTTTCCT CTCAGTCTTC TTATCTCGCC TATTATTATT                    40

( 2 ) INFORMATION FOR SEQ ID NO:27:

( i ) SEQUENCE CHARACTERISTICS:
    ( A ) LENGTH: 40 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:27:

GCGTGGGTTG GGGCCGGGAG GGCCAGCAGT CTCGTGCGTC                    40

( 2 ) INFORMATION FOR SEQ ID NO:28:

( i ) SEQUENCE CHARACTERISTICS:
    ( A ) LENGTH: 39 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:28:

CATTCATCTT CTCATTCTCG CCTAACTGTA CACATCTTT                     39

( 2 ) INFORMATION FOR SEQ ID NO:29:

( i ) SEQUENCE CHARACTERISTICS:
    ( A ) LENGTH: 39 base pairs ( B ) TYPE: nucleic acid
( C ) STRANDEDNESS: single
( D ) TOPOLOGY: linear ( x i ) SEQUENCE DESCRIPTION: SEQ ID NO:29:

GCGTGGGTTG GGGCCGGGAG GGCCAGCAGT CTCGTGCGT        39

( 2 ) INFORMATION FOR SEQ ID NO:30:

( i ) SEQUENCE CHARACTERISTICS:
    ( A ) LENGTH: 40 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:30:

GCGTGGGTTG GGGCCGGGAG GGCCAACAGT CTCGTGCGTC        40

( 2 ) INFORMATION FOR SEQ ID NO:31:

( i ) SEQUENCE CHARACTERISTICS:
    ( A ) LENGTH: 40 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:31:

CTACCCTTTC TTGACCACCG CCTCGTTTCA TCCACCTTAC        40

( 2 ) INFORMATION FOR SEQ ID NO:32:

( i ) SEQUENCE CHARACTERISTICS:
    ( A ) LENGTH: 40 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:32:

TTCTTTCTAT ACCCATATTA CCCTTCTTCA CACTCGTATC        40

( 2 ) INFORMATION FOR SEQ ID NO:33:

( i ) SEQUENCE CHARACTERISTICS:
    ( A ) LENGTH: 40 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:33:

CTTTATCCTT TCTCTTTCCT TGCACTCTAA CATCCTACTC        40

( 2 ) INFORMATION FOR SEQ ID NO:34:

( i ) SEQUENCE CHARACTERISTICS:
    ( A ) LENGTH: 40 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:34:

GCGTGGGTTG GGGCCGGTAG GGCCAGCAGT CTCGTTGCGT        40

( 2 ) INFORMATION FOR SEQ ID NO:35:

( i ) SEQUENCE CHARACTERISTICS:
    ( A ) LENGTH: 40 base pairs
    ( B ) TYPE: nucleic acid
    ( C ) STRANDEDNESS: single ( D ) TOPOLOGY: linear ( x i ) SEQUENCE DESCRIPTION: SEQ ID NO:35:

CCTTCTTGTT ATATTGGTCG TTTTCTTCTT TTACTTTCTT     40

( 2 ) INFORMATION FOR SEQ ID NO:36:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:36:

TCTTCATCAT TTCACTTCAT TCTGTCGGGC TATCTTCGGT     40

( 2 ) INFORMATION FOR SEQ ID NO:37:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:37:

TTCCACGTCT CCTCAGCCCG GGAGGCCACC TTTTTATCTG     40

( 2 ) INFORMATION FOR SEQ ID NO:38:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:38:

GAAGGCTTAA CCTAATTTTC CACCTTTCAT CCACTTTTCC     40

( 2 ) INFORMATION FOR SEQ ID NO:39:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:39:

TCACCTCCCA TTTATATTTT CCCTTAATTT CTTCTTCTTA     40

( 2 ) INFORMATION FOR SEQ ID NO:40:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:40:

CTTACTATGC ATCTTACTTA TTATTTTTTT TTACTTTCTA     40

( 2 ) INFORMATION FOR SEQ ID NO:41:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:41:

TACTTCTTTT ACATCATTCC TCGATTTATT CATTCTCCAC          40

( 2 ) INFORMATION FOR SEQ ID NO:42:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:42:

TTCACCCGTG TCATATCATA TTTCCCGGTC CTTCCTTTCC C          41

( 2 ) INFORMATION FOR SEQ ID NO:43:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:43:

CAATTCAAAC CTTTTCTACA ATTTTCATCT TACATTCTTC          40

( 2 ) INFORMATION FOR SEQ ID NO:44:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:44:

TCACTTGATC CTTCTTTACT TTTTTCTCG TCTAATTATA          40

( 2 ) INFORMATION FOR SEQ ID NO:45:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:45:

GCGTGGGTTG GGGCGGGATG GGCCAGCAGT CTCGTGCGGT          40

( 2 ) INFORMATION FOR SEQ ID NO:46:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:46:

CTTTTTATTC CAACCCCCAT TCTTACTTAC AATATCTTGA          40

( 2 ) INFORMATION FOR SEQ ID NO:47:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:47:

TATCCTTCTC CTTAACTCCT ACTTCTATCT ATAAAATTAT                        40

( 2 ) INFORMATION FOR SEQ ID NO:48:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:48:

GCGTGGGTAG GGGCCGGGAG GGCCAGCAGT CACGTGCGTA                        40

( 2 ) INFORMATION FOR SEQ ID NO:49:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:49:

GGGTGGGTTG GGGCCGGGAG GGCTAGCAGT CTCGTGCGTT                        40

( 2 ) INFORMATION FOR SEQ ID NO:50:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:50:

GCGTGGGATG GGGCCGGGAG GGCCAGCAGT CTCGTGCGTT                        40

( 2 ) INFORMATION FOR SEQ ID NO:51:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:51:

GCGTGGGTTG GGGCCGGGAG GGCCAGCAGT CTCGTGCGT                         39

( 2 ) INFORMATION FOR SEQ ID NO:52:

( i ) SEQUENCE CHARACTERISTICS:
        ( A ) LENGTH: 59 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:52:

TAGCGATACT GCGTGGGTTG GGGCGGGTAG GGCCAGCAGT CTCGTGCGGT             50

ACTTGAGCA                                                         59

( 2 ) INFORMATION FOR SEQ ID NO:53:

( i ) SEQUENCE CHARACTERISTICS:
        ( A ) LENGTH: 56 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:53:

| TAGCGATACT | GCGTGGGNGG | GNGGGNGGGC | CAGCAGTCTC | GTGCGGTACT | 50 |
| TGAGCA | | | | | 56 |

(2) INFORMATION FOR SEQ ID NO:54:

(i) SEQUENCE CHARACTERISTICS:
        (A) LENGTH: 87 base pairs
        (B) TYPE: nucleic acid
        (C) STRANDEDNESS: single
        (D) TOPOLOGY: linear (xi) SEQUENCE DESCRIPTION: SEQ ID NO:54:

| GCCGGATCCG | GGCCTCATGT | CGAANNNNNN | NNNNNNNNNN | NNNNNNNNNN | 50 |
| NNNNNNNNNN | NNNNTTGAGC | GTTTATTCTG | AGCTCCC | | 87 |

(2) INFORMATION FOR SEQ ID NO:55:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (xi) SEQUENCE DESCRIPTION: SEQ ID NO:55:

| CCGAAGCTTA | ATACGACTCA | CTATAGGGAG | CTCAGAATAA | ACGCTCAA | 48 |

(2) INFORMATION FOR SEQ ID NO:56:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:56:

| GCCGGATCCG | GGCCTCATGT | CGAA | 24 |

(2) INFORMATION FOR SEQ ID NO:57:

(i) SEQUENCE CHARACTERISTICS:
        (A) LENGTH: 87 base pairs
        (B) TYPE: nucleic acid
        (C) STRANDEDNESS: single
        (D) TOPOLOGY: linear (xi) SEQUENCE DESCRIPTION: SEQ ID NO:57:

| CCCCTGCAGG | TGATTTTGCT | CAAGTNNNNN | NNNNNNNNNN | NNNNNNNNNN | 50 |
| NNNNNNNNNN | NNNNNAGTAT | CGCTAATCAG | GCGGATC | | 87 |

(2) INFORMATION FOR SEQ ID NO:58:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (xi) SEQUENCE DESCRIPTION: SEQ ID NO:58:

| CCGAAGCTTA | ATACGACTCA | CTATAGGGAT | CCGCCTGATT | AGCGATACT | 49 |

(2) INFORMATION FOR SEQ ID NO:59:

(i) SEQUENCE CHARACTERISTICS:
        (A) LENGTH: 25 base pairs
        (B) TYPE: nucleic acid
        (C) STRANDEDNESS: single (D) TOPOLOGY: linear (x i) SEQUENCE DESCRIPTION: SEQ ID NO:59:

CCCCTGCAGG TGATTTTGCT CAAGT  25

NUCLEIC ACID LIGAND INHIBITORS OF HUMAN NEUTROPHIL ELASTASE

RELATED APPLICATIONS

This application is a divisional of U.S. application Ser. No. 08/199,507, filed Feb. 22, 1994, entitled Methods for Identifying Nucleic Acid Ligands of Human Neutrophil Elastase, now issued as U.S. Pat. No. 5,472,841. U.S. application Ser. No. 08/199,507 is a Continuation-in-Part of U.S. patent application Ser. No. 07/714,131, filed Jun. 10, 1991, entitled Nucleic Acid Ligands, now U.S. Pat. No. 5,475,096 which is a Continuation-in-Part of U.S. patent application Ser. No. 07/536,428, filed Jun. 11, 1990, entitled Systematic Evolution of Ligands by Exponential Enrichment, now abandoned, and U.S. patent application Ser. No. 07/964,624, filed Oct. 21, 1992 entitled Methods of Producing Nucleic Acid Ligands, now U.S. Pat. No. 5,496,938.

FIELD OF THE INVENTION

Described herein are high affinity nucleic acid ligands to human neutrophil elastase. The method utilized herein for identifying such nucleic acid ligands is called SELEX, an acronym for Systematic Evolution of Ligands by EXponential enrichment. Specifically disclosed herein are high-affinity nucleic acid ligands to elastase, including single-stranded RNA and single-stranded DNA ligands. Further included within the scope of this invention are modified nucleic acid ligands to elastase, specifically 2'-$NH_2$-modified RNA ligands, and mimetic ligands informed by the nucleic acid ligands identified herein.

BACKGROUND OF THE INVENTION

Human neutrophils store a battery of hydrolytic enzymes that are primarily utilized for the degradation of foreign substances during the phagocytosis process, one of the main host defense mechanisms against infectious agents. Human neutrophil elastase (hereinafter referred to as elastase) is a major protein stored in the azurophilic granules of human polymorphonuclear granulocytes (Dewald et al. (1975) J. Exp. Med. 141: 709) and secreted upon inflammatory stimuli (Bonney et al. (1989) J. Cell. Biochem. 39:47). Elastase is a single-chain glycoprotein 218 amino acids in length (Sinha et al. (1987) Proc. Natl. Acad. Sci. USA 84:2228). Elastase has two N-glycosylation sites at positions Asn-95 and Asn-144. Its molecular weight is about 29,500 daltons, and its isoelectric point (pI) lies between 8–9. The crystal structure of elastase complexed with an inhibitor has been determined (Navia et al. (1989) Proc. Natl. Aced. Sci. USA 86:7).

Elastase is a serine protease with broad substrate specificity and, therefore, is a voracious enzyme able to digest many macromolecules found in connective tissues. For example, elastase can hydrolyze macromolecules such as elastin, type III and type IV collagen, and fibronectin. In addition to connective tissue components, many plasma proteins such as immunoglobulins, clotting factors and complement proteins can also be hydrolyzed by elastase.

Neutrophil turnover and phagocytosis result in the leakage of enzymes into the extracellular matrix where they can cause damage to connective tissues. Natural inhibitors of elastase are made in the body to control the damaging process.

Excess elastase activity has been implicated in various disease states, such as pulmonary emphysema (Kaplan et al. (1973) J. Lab. Clin. Med. 82:349; Sanders and Moore (1983) Am. Rev. Respir. Dis. 127:554), cystic fibrosis, rheumatoid arthritis (Barrett (1978) Agents and Actions 8:11), chronic bronchitis, bronchopulmonary dysplasia in premature infants, and adult respiratory distress syndrome (ARDS) (Weiland et al. (1986) Am. Rev. Respir. Dis. 133:218). In most cases, the pathogenesis of these diseases has been correlated with the inactivation or the insufficiency of natural inhibitors of elastase, whose primary role is to keep excess enzyme activity under control. Several natural proteinase inhibitors have been shown to be effective in regulating the activity of elastase. Human $\alpha$-1-proteinase inhibitor ($\alpha$-1-PI) is the primary protease inhibitor found in plasma (Heimburger et al. (1970) in Proceedings of the First international Research Conference on Proteinase Inhibitors, Walter de Gruyter, New York, pp 1–21). In some individuals, $\alpha$-1-PI is present in unusually low amounts due to an underlying genetic defect; this low level causes familial emphysema (Garver et al. (1986) N. Engl. J. Med. 314:762). In other cases, the inhibitor is nonfunctional due to oxidative destruction by cigarette smoke (Janus et al. (1985) The Lancet i:152). Secretory leucocyte proteinase inhibitor (SLPI) is another elastase inhibitor found in all mucous secretions (Thompson & Ohlsson (1986) Proc. Natl. Acad. Sci. USA 83:6692) which is believed to be the major elastase inhibitor present in the upper airways of the lung. Recently, another natural elastase inhibitor, elafin, was characterized from human skin (Wiedow et al. (1990) J. Biol. Chem. 265:14791).

The development of elastase-specific inhibitors has been a major goal in the pharmaceutical industry for some time. As a result, different types of inhibitors have been developed. These include irreversible inhibitors such as peptide chloromethyl ketones (Powers et al. (1977) Biochim. Biophys. Acta 485:156), reversible inhibitors such as peptide boronic acids (Stone et al. (1990) Am. Rev. Respit. Dis. 141:47), cephalosporins (Doherty et al. (1986) Nature 322:192), and peptide aldehydes (Kennedy et al. (1987) Eur. J. Respit. Dis. 71:472). However, many of these inhibitors are nonspecific inhibitors of other serine proteases as well (Hemmi et al. (1985) Biochemistry 24:1841). Moreover, some of the more specific peptide-based inhibitors of elastase that have been developed suffer from a lack of oral availability (Williams et at. (1991) Am rev. Respir. Dis. 144:875). Some of the β-lactam inhibitors have both stability problems and lack oral availability (Knight et al. (1992) Biochemistry 31:4980). In addition to synthetic inhibitors, biosynthetically derived naturally occurring inhibitors such as $\alpha$-1-proteinase (Gadek et al. (1981) J. Clin. Invest. 68:1158), eglin C (Snider et al. (1985) Am. Rev. Respir. Dis. 132:1155), and SLPI (Gauthier et al. (1982) Biochim. Biophys. Acta 700:178; Gast et al. (1990) Am. Rev. Respir. Dis. 141: 889) are under development.

Polynucleotides including synthetic RNA homopolymers (Simon et al. (1988) Exp. Lung Res. 14:85), tRNAs and DNAs (Lestienne & Bieth (1983) Biochimie 65:49) have been shown to inhibit elastase to some extent. The enzyme inhibition caused by these polyanions is not likely due to simple electrostatic interactions, because other polyanions lacking hydrophobic constituents such as heparin and polyanionic polysaccharides have been shown to be ineffective inhibitors. Cell extracts of certain pneumococcal species (Pneumococci type I, type II smooth, and type II rough) yield high molecular weight RNAs upon autolysis that act as elastase inhibitors (Vered et al. (1988) Exp. Lung Res. 14:67).

A method for the in vitro evolution of nucleic acid molecules with high affinity binding to target molecules has been developed. U.S. patent application Ser. No. 07/536, 428, filed Jun. 11, 1990, entitled Systematic Evolution of Ligands by Exponential Enrichment, now abandoned, and U.S. Pat. No. 5,270,163, issued Dec. 14, 1993, and U.S. patent application Ser. No. 07/714,131, filed Jun. 10, 1991, now U.S. Pat. No. 5,475,096, both entitled Nucleic Acid Ligands (See also WO91/19813) describe a fundamentally novel method for making a nucleic acid ligand for any desired target. Each of these applications, collectively referred to herein as the SELEX Patent Applications, is specifically incorporated herein by reference.

The SELEX method involves selection from a mixture of candidate oligonucleotides and step-wise iterations of the same general selection theme, to achieve virtually any desired criterion of binding affinity and selectivity. Starting with a mixture of nucleic acids, preferably comprising a segment of randomized sequence, the SELEX method includes steps of contacting the mixture with the target under conditions favorable for binding, partitioning unbound nucleic acids from those nucleic acids which have bound to target molecules, dissociating the nucleic acid-target complexes, amplifying the nucleic acids dissociated from the nucleic acid-target complexes to yield a ligand-enriched mixture of nucleic acids, then reiterating the steps of binding, partitioning, dissociating and amplifying through as many cycles as desired to yield high affinity nucleic acid ligands to the target molecule.

The basic SELEX method may be modified to achieve specific objectives. For example, U.S. patent application Ser. No. 07/960,093, filed Oct. 14, 1992, entitled Method for Selecting Nucleic Acids on the Basis of Structure, describes the use of SELEX in conjunction with gel electrophoresis to select nucleic acid molecules with specific structural characteristics such as bent DNA. U.S. patent application Ser. No. 08/123,935, filed Sep. 17, 1993, entitled Photoselection of Nucleic Acid Ligands, describes a SELEX based method for selecting nucleic acid ligands containing photoreactive groups capable of binding and/or photocrosslinking to and/ or photoinactivating a target molecule. U.S. patent application Ser. No. 08/134,028, filed Oct. 7, 1993, entitled High-Affinity Nucleic Acid Ligands That Discriminate Between Theophylline and Caffeine, describes a method for identifying highly specific nucleic acid ligands able to discriminate between closely related molecules, termed "counter-SELEX". U.S. patent application Ser. No. 08/143,564, filed Oct. 25, 1993, entitled Systematic Evolution of Ligands by EXponential Enrichment: Solution SELEX, describes a SELEX-based method which achieves highly efficient partitioning between oligonucleotides having high and low affinity for a target molecule.

The SELEX method encompasses the identification of high-affinity nucleic acid ligands containing modified nucleotides conferring improved characteristics on the ligand, such as improved in vivo stability or delivery. Examples of such modifications include chemical substitutions at the ribose and/or phosphate and/or base positions. SELEX-identified nucleic acid ligands containing modified nucleotides are described in U.S. patent application Ser. No. 08/117,991, filed Sep. 8, 1993, entitled High Affinity Nucleic Acid Ligands Containing Modified Nucleotides, which describes oligonucleotides containing nucleotide derivatives chemically modified at the 5- and 2'-positions of pyrimidines, as well as specific RNA ligands to thrombin containing 2'-amino modifications. U.S. patent application Ser. No. 08/134,028, supra, describes nucleic acid ligands to theophylline and caffeine containing one or more nucleotides modified with 2'-amino (2'-$NH_2$), 2'-fluoro (2'-F), and/or 2'-Omethyl (2'-OMe).

The development of high affinity ligands capable of inhibiting elastase would be useful in the treatment of diseases such as pulmonary emphysema (Kaplan et al. (1973) supra; Sanders and Moore (1983) supra), cystic fibrosis, rheumatoid arthritis (Barrett (1978) supra), chronic bronchitis, bronchopulmonary dysplasia in premature infants, and adult respiratory distress syndrome (ARDS) (Weiland et al. (1986) supra). Herein described are high affinity nucleic acid ligand inhibitors of elastase.

BRIEF SUMMARY OF THE INVENTION

Described herein are nucleic acid ligands to human neutrophil elastase identified through the SELEX procedure. This invention includes 2'-$NH_2$ RNA, and single-stranded DNA ligands to elastase. Included within the invention are the 2'-$NH_3$ RNA sequences shown in Table 1. Further included within the invention are the DNA sequences shown in Table 6.

This invention also includes nucleic acid ligands which inhibit the biological activity of elastase.

Further included in this invention is a method of identifying nucleic acid ligands and ligand sequences to elastase comprising the steps of a) contacting a candidate mixture of single-stranded nucleic acids with elastase, wherein nucleic acids having an increased affinity to elastase relative to the candidate mixture may be partitioned from the remainder of the candidate mixture; b) partitioning the increased affinity nucleic acids from the remainder of the candidate mixture; and c) amplifying the increased affinity nucleic acids to yield a ligand-enriched mixture of nucleic acids, whereby nucleic acid ligands to elastase may be identified.

BRIEF DESCRIPTION OF THE FIGURES

FIGS. 8A and 8B show the predicted secondary structure of the G-quartet sequence (SEQ ID NO:7).

FIG. 12 shows the 2'-$NH_2$-RNA SELEX primer-template constructs (Primer-Template-Mixture I) and ssDNA SELEX primer template constructs (Primer-Template-Mixture (II).

DETAILED DESCRIPTION OF THE INVENTION

Figure 1:
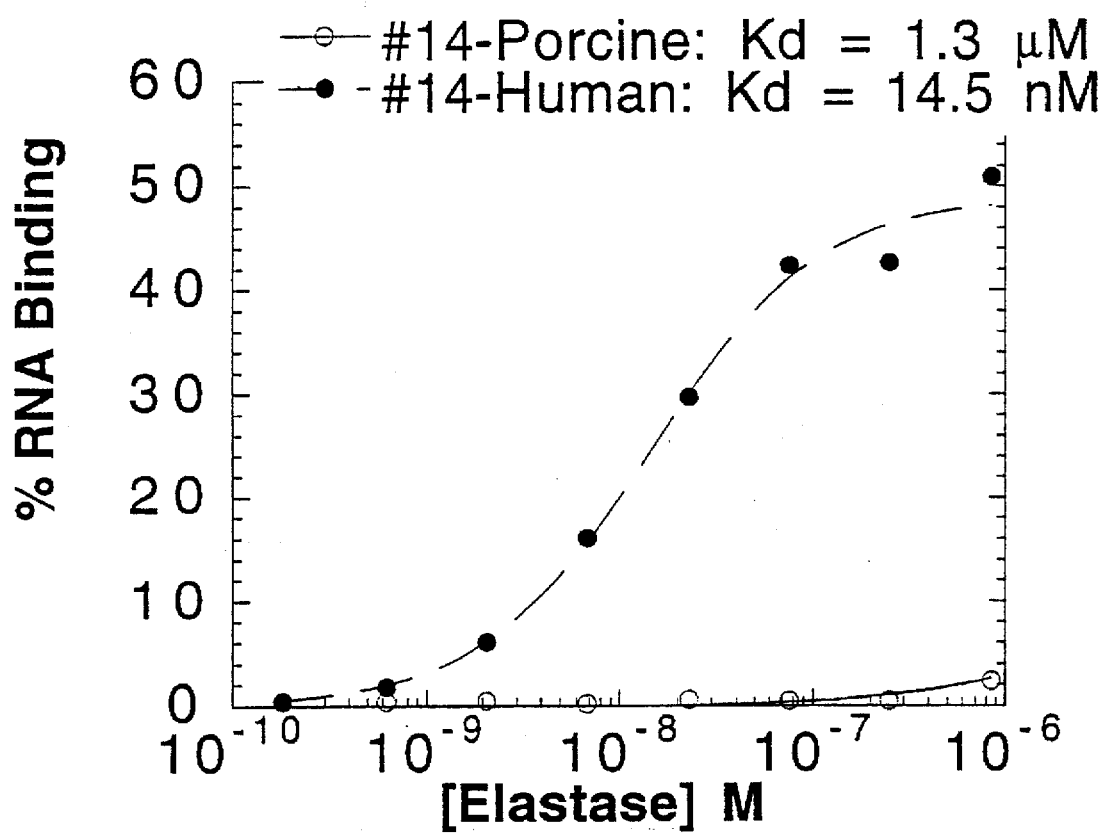
FIG. 1 shows the binding of representative ligand 14 (SEQ ID NO:10) to human (●)(Kd=14.5 nM) and porcine (o) (Kd=1.3 µM) elastase wherein elastase concentrations were varied from $10^{-10}$ to $10^{-6}$M.

This application describes high-affinity nucleic acid ligands to elastase identified through the method known as SELEX. The SELEX method is described in detail in U.S. patent application Ser. No. 07/714,131 filed Jun. 10, 1991 entitled Nucleic Acid Ligand, now U.S. Pat. No. 5,475,096, and Ser. No. 07/536,428 filed Jun. 11, 1990 entitled Systematic Evolution of Ligands by EXponential Enrichment, now abandoned. The full text of these applications, including but not limited to, all definitions and descriptions of the SELEX process, are specifically incorporated herein by reference.

In its most basic form, the SELEX process may be defined by the following series of steps:

1) A candidate mixture of nucleic acids of differing sequence is prepared. The candidate mixture generally includes regions of fixed sequences (i.e., each of the members of the candidate mixture contains the same sequences in the same location) and regions of randomized sequences. The fixed sequence regions are selected either: a) to assist in the amplification steps described below; b) to mimic a sequence known to bind to the target; or c) to enhance the concentration of a given structural arrangement of the nucleic acids in the candidate mixture. The randomized sequences can be totally randomized (i.e., the probability of finding a base at any position being one in four) or only partially randomized (e.g., the probability of finding a base at any location can be selected at any level between 0 and 100 percent).

2) The candidate mixture is contacted with the selected target under conditions favorable for binding between the target and members of the candidate mixture. Under these circumstances, the interaction between the target and the nucleic acids of the candidate mixture can be considered as forming nucleic acid-target pairs between the target and those nucleic acids having the strongest affinity for the target.

3) The nucleic acids with the highest affinity for the target are partitioned from those nucleic acids with lesser affinity to the target. Because only an extremely small number of sequences (and possibly only one molecule of nucleic acid) corresponding to the highest affinity nucleic acids exist in the candidate mixture, it is generally desirable to set the partitioning criteria so that a significant amount of the nucleic acids in the candidate mixture (approximately 5–50%) are retained during partitioning.

4) Those nucleic acids selected during partitioning as having relatively higher affinity to the target are then amplified to create a new candidate mixture that is enriched in nucleic acids having a relatively higher affinity for the target.

5) By repeating the partitioning and amplifying steps above, the newly formed candidate mixture contains fewer and fewer unique sequences, and the average degree of affinity of the nucleic acids to the target will generally increase. Taken to its extreme, the SELEX process will yield a candidate mixture containing one or a small number of unique nucleic acids representing those nucleic acids from the original candidate mixture having the highest affinity to the target molecule.

The SELEX Patent Applications describe and elaborate on this process in great detail. Included are targets that can be used in the process; methods for the preparation of the initial candidate mixture; methods for partitioning nucleic acids within a candidate mixture; and methods for amplifying partitioned nucleic acids to generate enriched candidate mixtures. The SELEX patent applications also describe ligand solutions obtained to a number of target species, including protein targets wherein the protein is or is not a nucleic acid binding protein.

SELEX provides high affinity ligands of a target molecule. This represents a singular achievement that is unprecedented in the field of nucleic acids research. The present invention applies the SELEX procedure to the specific target of human neutrophil elastase. In the Example section below, the experimental parameters used to isolate and identify the nucleic acid ligand solutions to elastase are described.

In order to produce nucleic acids desirable for use as a pharmaceutical, it is preferred that the nucleic acid ligand 1) binds to the target in a manner capable of achieving the desired effect on the target; 2) be as small as possible to obtain the desired effect; 3) be as stable as possible; and 4) be a specific ligand to the chosen target. In most, if not all, situations it is preferred that the nucleic acid ligand have the highest possible affinity to the target.

In co-pending and commonly assigned U.S. patent application Ser. No. 07/964,624, filed Oct. 21, 1992 ('938), methods are described for obtaining improved nucleic acid ligands after SELEX has been performed. The '938 patent, entitled Methods of Producing Nucleic Acid Ligands, is specifically incorporated herein by reference.

The present invention includes the specific 2'-$NH_2$ RNA ligands of elastase shown in Table 1. The scope of the ligands covered by this invention extends to all RNA ligands of elastase, modified and unmodified, identified according to the SELEX procedure, and further, ligands obtained by use of the ligands of the present invention. More specifically, this invention includes nucleic acid sequences that are substantially homologous to and that have substantially the same ability to bind elastase as the specific nucleic acid ligands shown in Table 1. By substantially homologous, it is meant, a degree of primary sequence homology in excess of 70%, most preferably in excess of 80%. Substantially the same ability to bind elastase means that the affinity is within one to two orders of magnitude of the affinity of the ligands described herein. It is well within the skill of those of ordinary skill in the art to determine whether a given sequence—substantially homologous to those specifically described herein—has substantially the same ability to bind elastase.

This invention includes the specific DNA ligands of elastase shown in Table 6, identified by the method described in Example 1. The scope of the ligands covered by this invention extends to all DNA ligands of elastase, modified and unmodified, identified according to the SELEX procedure, and further, ligands obtained by use of the ligands of the present invention. More specifically, this invention includes nucleic acid sequences that are substantially homologous to and that have substantially the same ability to bind elastase as the specific nucleic acid ligands shown in Table 6.

This invention encompasses the use of the disclosed ligands to identify a second ligand. In one embodiment, a first SELEX identified ligand which binds to a specific site of the target molecule is used to elute secondary ligands binding to the same site. In another embodiment, a first SELEX identified ligand binding to a specific site of the target molecule is used to select secondary ligands which do not bind to the same site. In this case, SELEX is conducted in the presence of the first ligand such that the binding site is saturated with the first ligand and selection occurs for ligands binding elsewhere on the target molecule. In a further embodiment analogous to the generation of anti-idiotype antibodies, a SELEX identified ligand to elastase may itself be used as a target molecule to identify secondary ligands resembling the elastase binding site. Such secondary ligands may compete with elastase-substrate binding and inhibit the biological activity of elastase.

A review of the sequence homologies of the RNA ligands of elastase shown in Table 1 or the DNA ligands shown in Table 6 shows that sequences with little or no primary homology may have substantially the same ability to bind elastase. For these reasons, this invention also includes nucleic acid ligands that have substantially the same three dimensional structure as the ligands presented herein and substantially the same ability to bind elastase as the nucleic acid ligands shown in Tables 1 and 6.

The present invention identifies and describes $2'$-$NH_2$-modified RNA ligands which inhibit elastase activity (Example 3). Several of these inhibitory ligands were truncated by removal of the 3'-fixed sequence and the ability of the truncated ligands to inhibit elastase examined (Example 4). Based on primary sequence homology, the ligands of elastase have been grouped into a number of classes. The results show that for class I and II ligands, 3'-truncated ligands had similar abilities to inhibit elastase as the full-length ligands. However, for class III and IV ligands, the 3'-fixed sequence truncated ligands lost their ability to inhibit elastase.

The effect that the presence of small monovalent cations such as $K^+$ and $Li^+$ on affinity of ligands to elastase was examined (Example 5). The results suggest that $K^+$ may favor the formation of higher affinity secondary structures than $Li^+$.

Effect of pH on Binding. The overall effect of pH on ligand binding involves an interplay of factors contributed both by the protein and the ligand. In order to isolate the factors contributed by elastase, the binding of a single-stranded DNA (ssDNA) ligand to elastase was examined wherein the effect of pH on binding should derive primarily from the effect of pH on elastase (Example 6). The ssDNA ligand bound better at a low pH, and the Kd of binding increased approximately two fold over two pH units. In contrast, the binding of the $2'$-$NH_2$ RNA ligand-to elastase was profoundly affected by pH. The Kd of the binding increased more than 10 fold when the pH was decreased from 6.5 to 6.25. The optimum binding for the $2'$-$NH_2$-modified RNA ligand to elastase was at pH 7.0, the pH at which SELEX was conducted.

The observation that binding of the $2'$-$NH_2$ modified RNA ligands is pH dependent effects how the ligands may best be utilized. For example, by using two buffers with different pHs, it may be possible to develop two ligands for a given target, each of which binds at a different pH. Likewise, one may tailor ligands with high affinity binding for a given target molecule in one cell compartment with specific pH, but not to the same protein in another cell compartment with a different pH. Similarly, ligands that are active specifically in certain cell types, for example tumor cells which are known to have lower internal pH than normal cells, may be discovered with $2'$-$NH_2$ modified RNAs.

Figure 11:
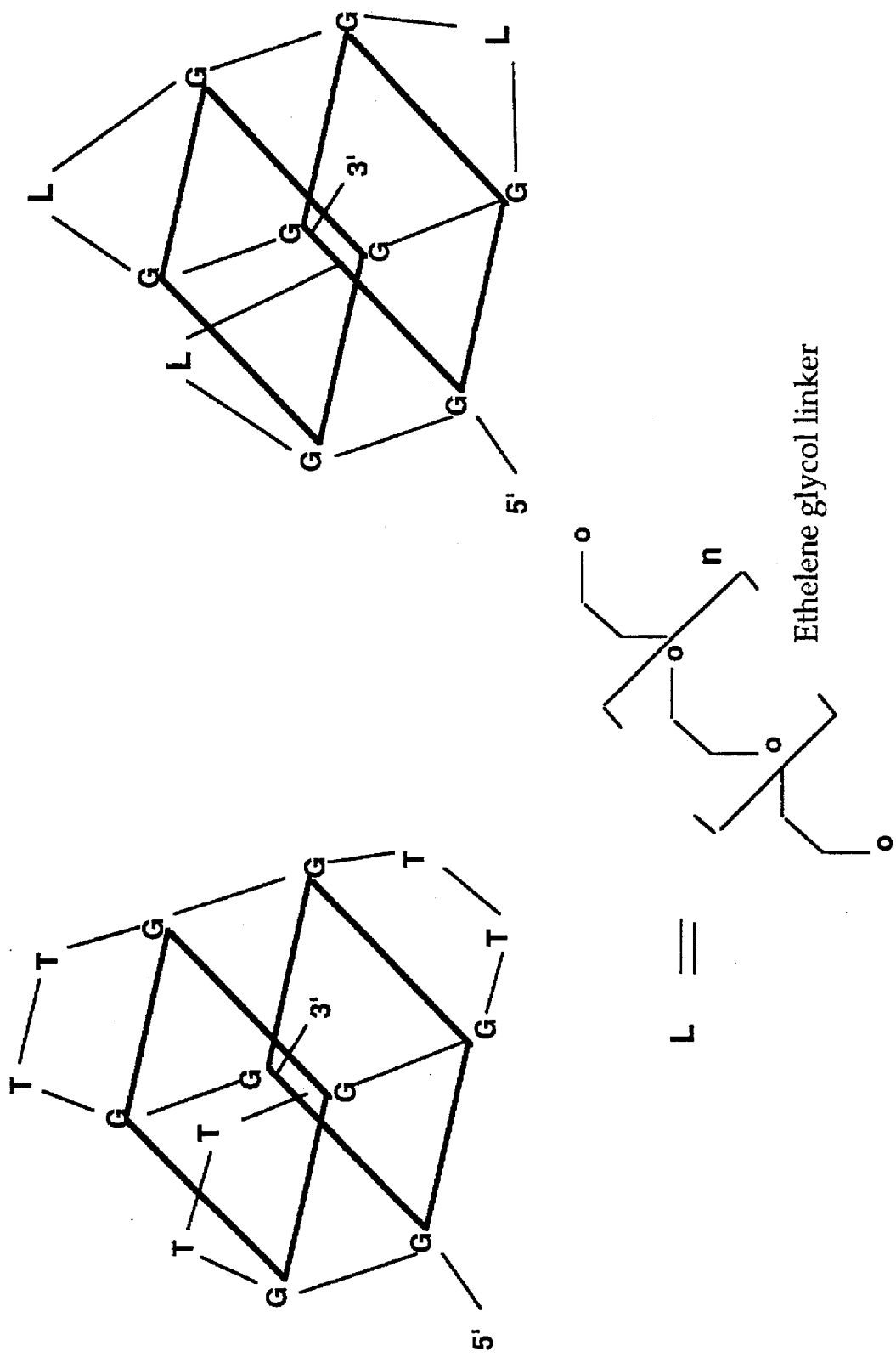
FIG. 11 shows a predicted G-quartet structure and the mimetic molecule wherein the connecting loop nucleotides are replaced by a synthetic ethylene glycol linker tether.

Nucleic Acid Mimetics. Several classes of elastase ligands identified herein appear to assume a "G-quartet" type structure. Sequences rich in repeated runs of contiguous guanines undergo structural rearrangement to form planar quartets joined by Hoogstein hydrogen bonds of four guanine residues. Based on X-ray fiber diffraction data, a G-quartet was described for poly rG (Zimmerman et al. (1975) J. Mol. Biol. 92:181–192). In the late 1980s, this structure was identified in DNA sequences containing short runs of guanines interrupted by several bases, and such DNA sequences are found in immunoglobulin switch regions (Sen, D. and Gilbert, W. (1988) Nature 334:364–366) and in telomeres (Williamson et al. (1989) Cell 59:871–880). The G-quartet structure can occur within a single DNA strand (intramolecular G-quartet) or between two (Sundquist et al. (1989) Nature 342:825–829; Kang et al. (1992) Nature 356:126–131) or four strands (intermolecular G-quartets) (Sen and Gilbert (1988) supra). After the initial report on G-quartet structure on the homopolymer, poly rG, much attention on the structure has been focussed on DNA. However, in recent reports (Sundquist and Heaphy (1993) Proc. Natl. Acad. Sci. USA 90:3393–3397; Awang and Sen (1993) Biochemistry 32:11453–11457) the G-quartet structure has been identified in heterogenous RNA molecules such as HIV-1 genomic RNA. Nucleic acid ligands with G-quartet structures are attractive candidates for developing nucleic acid mimetic molecules. The replacement of connecting loop nucleotides by a synthetic linker as a possible basic modification in an intramolecular tetraplex was examined in Example 7. In such a molecule, the synthetic tether should allow the folding to assume a G-quartet structure; as shown in FIG. 11.

EXAMPLE 1

Material and Methods

Elastase. Human neutrophil elastase was purchased from Athens Research and Technology, Athens, Ga. All oligodeoxynucleotides were synthesized at Operon Technologies by standard chemistry employing cyanoethyl phosphoramidites.

$2'$-$NH_2$ RNA SELEX. Essential features of the SELEX protocol have been described in detail in U.S. patent application Ser. No. 07/714,131 filed Jun. 10, 1991, now U.S. Pat. No. 5,475,096, U.S. patent application Ser. No. 07/964,624 filed Oct. 21, 1992, now U.S. Pat. No. 5,496,938, and in several references (Tuerk & Gold (1990) Science 249:505; Tuerk et al. (1992) Proc. Natl. Acad. Sci. USA 89:6988; Tuerk et al. (1992b) in Polymerase Chain Reaction (Ferre, F, Mullis, K., Gibbs, R. & Ross, A., eds.) Birkhauser, N.Y.). The random nucleotides of the initial candidate mixture were comprised of $2'$-$NH_2$ pyrimidine and $2'$-OH purine bases. All RNA synthesizing steps by in vitro transcription were conducted with $2'$-$NH_2$ pyrimidine bases.

Briefly, the first round random pool of RNA was derived from the transcription of a DNA template containing a forty-nucleotide random region flanked by defined regions;

the complexity of the pool was in the order of $10^{14}$ molecules. The DNA template and the corresponding PCR primers were synthesized chemically by standard techniques using cyanoethyl phosphoramidites (Operon). The random region was generated by reacting with all four phosphoramidites at optimized concentrations of each to obtain equimolar coupling during oligonucleotide synthesis. Defined nucleotide sequences in the flanking regions of the template served as primer annealing sites for PCR, for reverse transcriptase and as a promoter for T7 RNA polymerase, and restriction enzyme sites that allow cloning into vectors.

The SELEX was done with the primer-template mixture I, as shown in FIG. 12. 2'-$NH_2$ RNA transcriptions were carried out in 100 µl transcription reactions containing 2 mM each ATP, GTP, 2'-$NH_2$CTP and 2'-$NH_2$-UTP, 40 mM Tris-HCl (pH 8.0), 12 mM $MgCl_2$, 1 mM Spermidine, 5 mM DTT, 0.002% Triton X-100 and 4% polyethylene glycol (w/v) at room temperature for 2 hr. The full length transcripts were gel purified, resuspended in binding buffer [150 mM NaCl, 100 mM Tris-HCl (pH 7.0), 2 mM $MgCl_2$ and 6 mM KCl], heated to 70° C. for 3 min., chilled on ice, and incubated with HNE at 37° C. for 10 min.

The RNA pool was incubated with elastase (1.7–0.003 µM) in binding buffer containing 150 mM NaCl, 100 mM Tris-HCl (pH 7.0), 2 mM $MgCl_2$, and 6 mM KCl for 10 minutes at 37° C. The RNA-protein mixture was passed through a nitrocellulose filter (0.45µ, Millipore) and the RNA from RNA-protein complexes retained on the filter was eluted (Tuerk & Gold (1990) supra) and recovered. The recovered RNA was reverse transcribed into cDNA by AMV reverse transcriptase at 48° C. The resulting cDNA was amplified by PCR and the amplified DNA used as the template for T7 RNA polymerase to obtain a pool of RNA for the subsequent round of SELEX. To avoid the selection and amplification of undesired nitrocellulose binding RNA molecules, the newly transcribed RNA pool was passed through several layers of nitrocellulose filters (negative selection) before the next round of selection with HNE. The procedure was reiterated until the enriched pool of RNA showed significantly improved affinity to elastase over the initial random pool.

Once significant binding of the 2'-$NH_2$ RNA pool was achieved, PCR-amplified DNA was digested with HindIII and BamHI, and cloned into pUC18 previously digested with the same enzymes by standard techniques (Tuerk & Gold (1990) supra). Recombinant plasmids were isolated and sequenced.

Single-Stranded DNA SELEX. SELEX was conducted with a candidate library of single-stranded DNA (ssDNA) molecules. The SELEX experiment was carried out by using the primer template-mixture II, as shown in FIG. 12. Briefly, after nitrocellulose filter partitioning, filter bound ssDNA was recovered by incubating the filter in a mixture of neutralized phenol and 7M urea at 37° C. followed by extraction of the aqueous phase. Recovered ssDNA was precipitated with ethanol, and an aliquot used as a template in a PCR reaction to identify the optimum number of cycles needed to produce double-stranded DNA (dsDNA) molecules of the correct size without creating high molecular weight DNAs. The optimum number of cycles was used for a bulk PCR reaction (800 µl) carried out with the remaining recovered ssDNA as the template and a biotinylated primer (BiO-3G2) and a non-biotinylated primer (5G2). The PCR products are gel purified to remove unincorporated biotinylated primer. The non-biotinylated strand of the double-stranded DNA was isolated from the complementary strand by incubation of the PCR product with 200 µl of streptavidin beads (Pierce) followed by alkali denaturation (0.15N NaOH, 30 min at room temperature). The recovered single-stranded DNA was neutralized, precipitated with ethanol, and used for the next round of SELEX. The recovery of ssDNA by streptavidin capture was about 30–40%.

The use of biotinylated primer 3G2 and the non-biotinylated primer 5G2 in PCR yields the bottom DNA strand after streptavidin capture. Therefore, to obtain a fairly large sequence space for the first round of SELEX, 10 nm of HPLC-purified synthetic bottom strand was used. For each SELEX round, a small fraction of ssDNA was end-labelled, gel purified, and used for a mini-binding curve with three different elastase concentrations. These results were then used to obtain the protein concentration at which 5–10% of the DNA remains on the filter above the background level used for the subsequent round.

Except for the first round, selected ssDNA was passed through a layer of 4–5 nitrocellulose filters after every SELEX round to remove those DNA molecules that bound to the filter, not elastase (filter binders). However, even after this prefiltration treatment, the percentage of filter binders increased from 0.2% to as high as 12–15%. To avoid the high background problem, the filters were washed with 0.5M urea solution immediately after the filtration of the protein-DNA mixture. The urea treatment brought background binding levels to 0.1–0.2%. Therefore, during each SELEX round as well as during determination of binding curves, the filters were washed with 10 ml of 0.5M urea and 10 ml of binding buffer.

Several polyanions including tRNA have been shown to bind and inhibit elastase (Lestienne and Bieth (1983) supra). In order to increase the stringency of selection, tRNA at a concentration 8–10 times higher than that of ssDNA was included in the binding reaction as a competitor after the 9th SELEX round. The apparent Kd of random ssDNA was determined to be approximately 0.25 µm, whereas the Kd of ssDNA after 14 SELEX rounds was 22 nM.

Elastase Inhibition Assay. The assay for elastase inhibition is based on the use of a chromogenic tetrapeptide substrate. The assay was conducted in a solution containing 10 nM elastase, 0.5 mM N-methoxysuccinyl-Ala-Ala-Pro-Val-p-nitroanilide, 150 mM NaCl, 26mM KCl, 2 mM $MgCl_2$, 0.02% HSA, 0.05% DMSO, 0.01% Triton X-100, and 100 mM Tris-HCl, at 25° C. The assay measured by spectroscopy (OD 405 nm) the generation of elastase-induced release of p-nitroanilide as a function of time. The rate of p-nitroanilide generation in the absence of inhibitor was used as the negative control; the positive control contained the irreversible inhibitor N-methoxysuccinyl-Ala-Ala-Pro-Val-chloromethyl ketone. OD values were plotted against time, and the slope used to determine the rate of enzyme activity.

Cell detachment assay. An assay was developed in which elastase-induced endothelial cell detachment is measured in cultured endothelial cells. Endothelial cells were grown under standard culture conditions in 24-well plates to obtain a confluent monolayer. The cells were washed with solution A (PBS, 20 mM HEPES, 10 mM glucose) prior to addition of elastase with and without the test ligand. After incubation at 37° C. for 45 minutes, the supernatant was removed and counted for detached cells.

EXAMPLE 2

2'-$NH_2$ RNA SELEX

SELEX was conducted as described above for 17 rounds. The resulting affinity of the enriched pool to elastase was significantly improved (dissociation constant (Kd) of about 70 nM as compared to the unselected random pool having a Kd of 0.8 µM). At this point, PCR-amplified DNA was cloned and sixty individual clones were sequenced (Table 1). Ligands were grouped into classes on the basis of primary sequence homology. Kds of representative ligands belonging to different classes are shown in Table 2.

Specificity of ligands. As shown in Table 3, 2'-NH$_2$ ligands to elastase did not exhibit high affinity binding to other proteins such as thrombin and basic fibroblast growth factor (bFGF). The specificity of the ligands to human elastase was tested by comparing representative ligand 14 (SEQ ID NO:10) binding to human and porcine elastase. The homology between these proteins is about 40% overall, but the sequences are essentially identical in the catalytic region. As shown in FIG. 1, ligand 14 did not bind porcine elastase at a detectable level at any concentrations.

EXAMPLE 3

Identification of Inhibitory Ligands to Elastase

Figure 2:
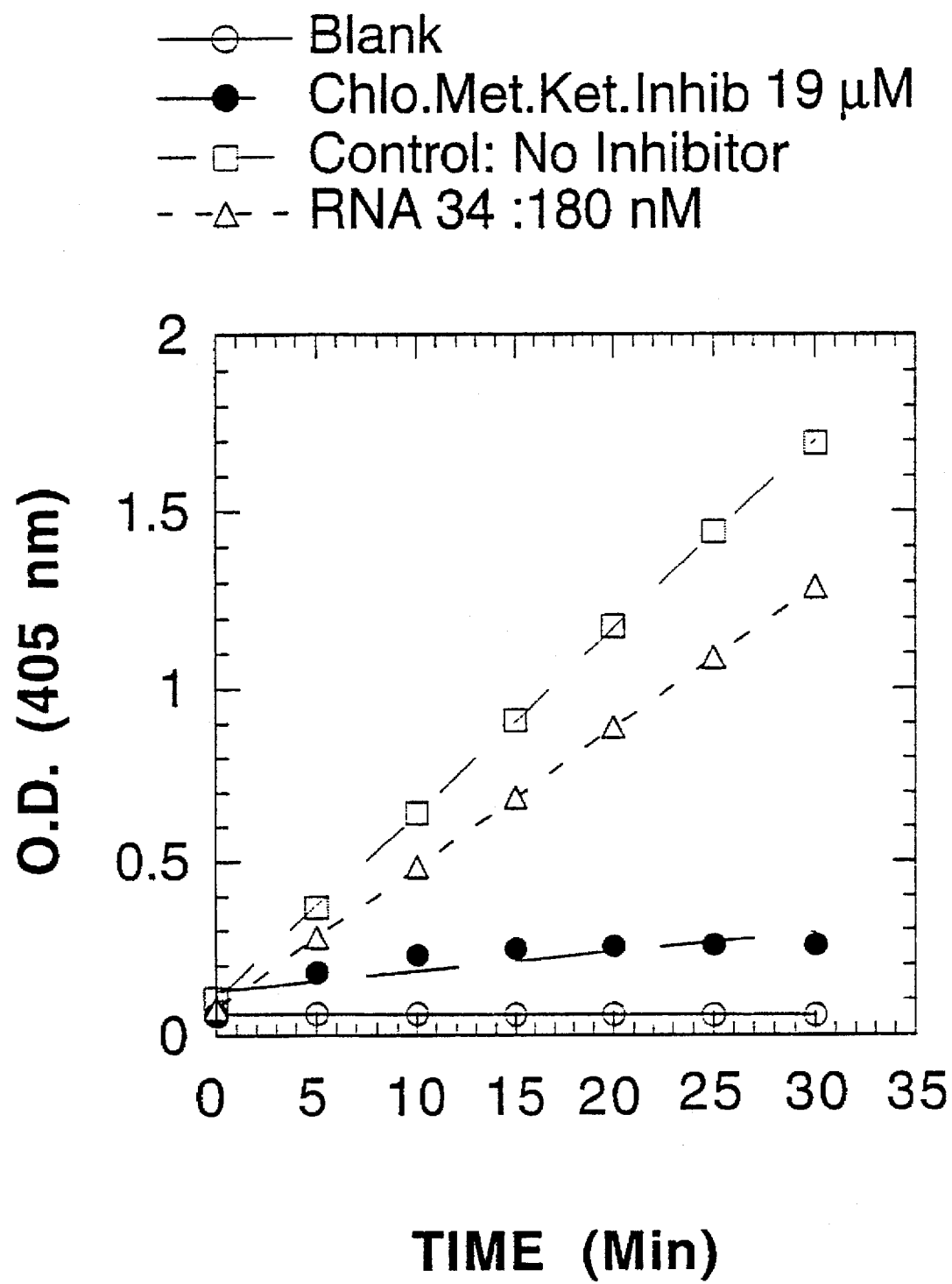
FIG. 2 shows the elastase inhibitory activity of representative ligand 34 (SEQ ID NO:7). Generation of p-nitroanilide was measured in the absence of elastase (o), in the presence of the irreversible inhibitor N-methoxysuccinyl-Ala-Ala-Pro-Val-chloromethyl ketone (●, in the absence of any inhibitor (□), and in the presence of 180 nM ligand 34 (◊).

Using the elastase inhibition assay described in Example 1, several ligands with inhibitory activity toward elastase were identified. Molecules belonging to class I and II were found to inhibit elastase. Clone 9 of class III and clone 19 of class IV also exhibited inhibitory activity. FIG. 2 shows the elastase inhibitory activity of representative ligand 34. The elastase inhibitory activity of all RNA ligands tested was dependent on RNA concentration, and had a maximum inhibition of elastase of approximately 30%.

Figure 3A:
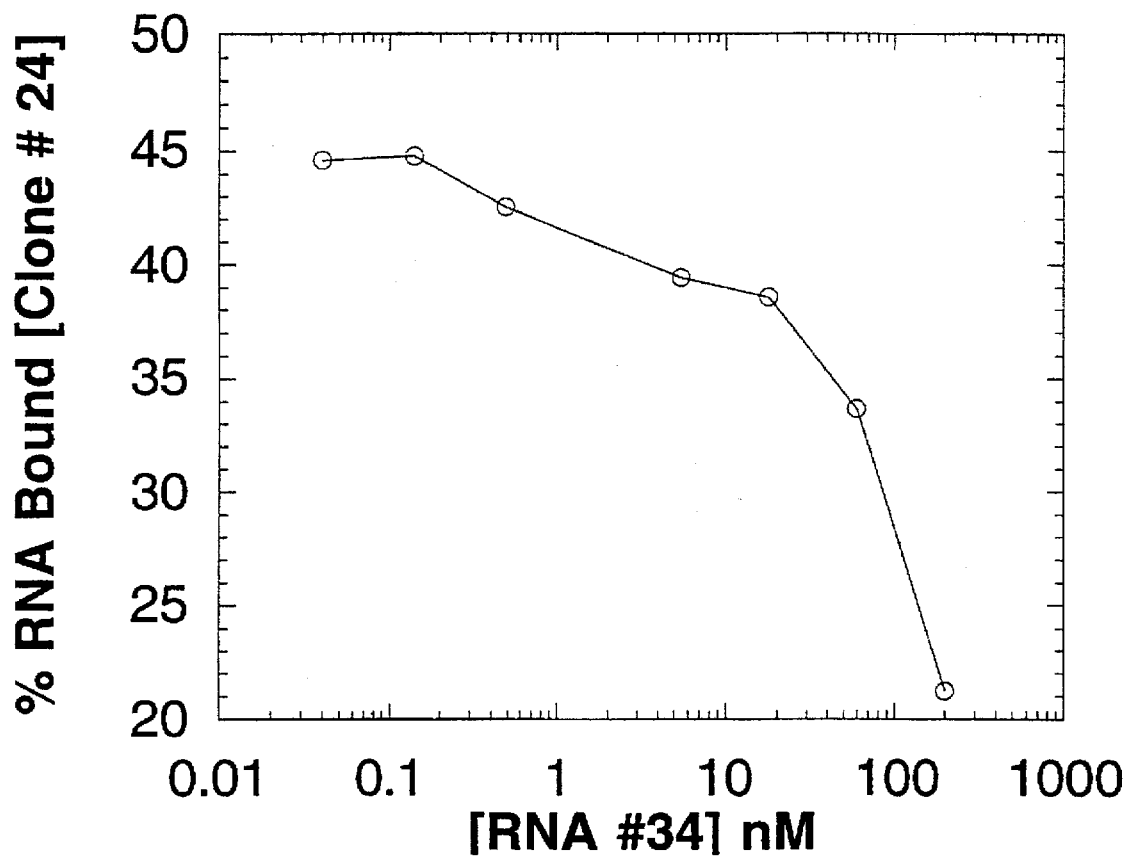
FIG. 3a shows the results of competition experiments carried out between ligands 24 (SEQ ID NO:8) and 30 (SEQ ID NO:1) (Classes I and II).
Figure 3B:
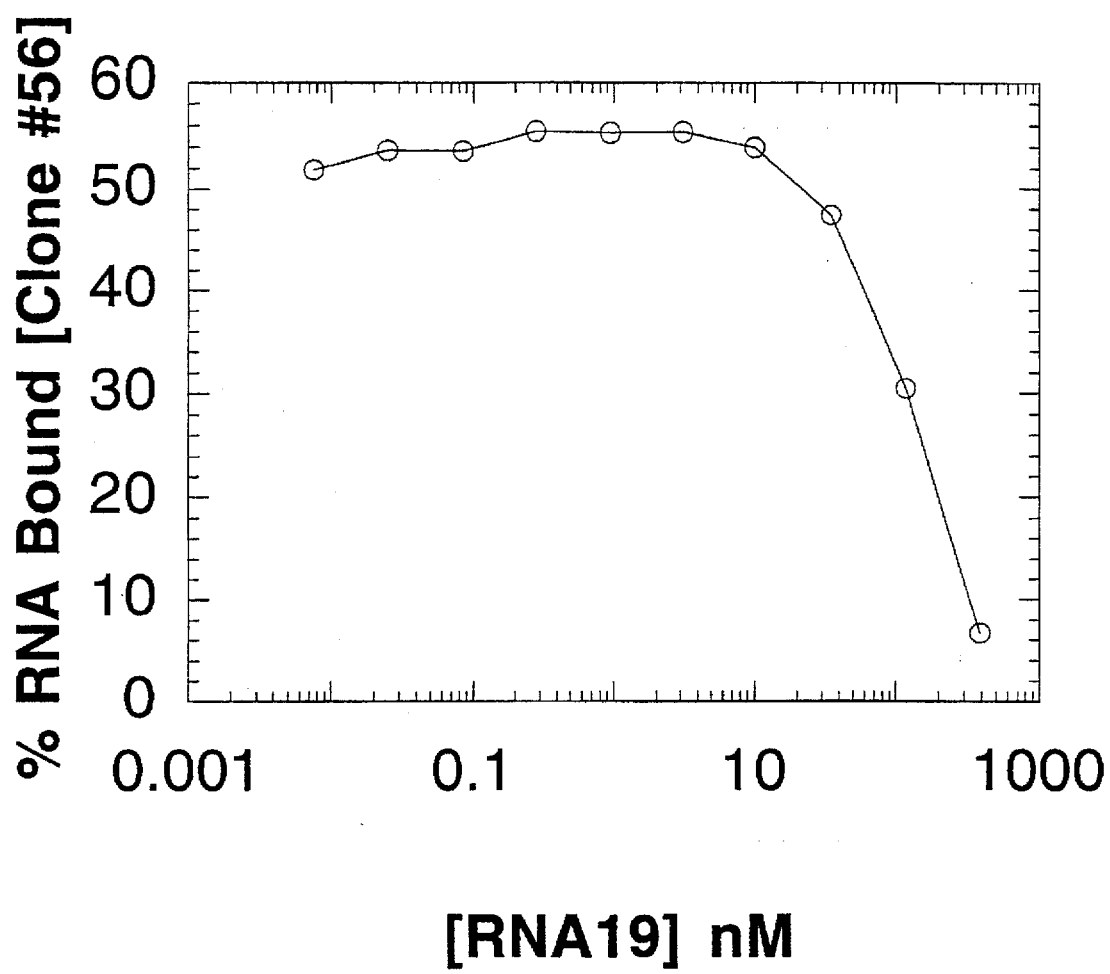
FIG. 3b shows the results of competition experiments carried out between ligands 56 (SEQ ID NO:5) and 19 (SEQ ID NO:15) (Classes II and IV).

Since ligands from different classes exhibited similar inhibition of elastase, competition experiments were conducted with ligands 24 and 30 (class I and II) and ligands 56 and 19 (class II and IV), to determine if these ligands competed with each other. The results (FIGS. 3a and 3b) indicate that these ligands appear to compete with each other for the same binding site of the elastase protein or for spatially close binding sites.

Figure 4:
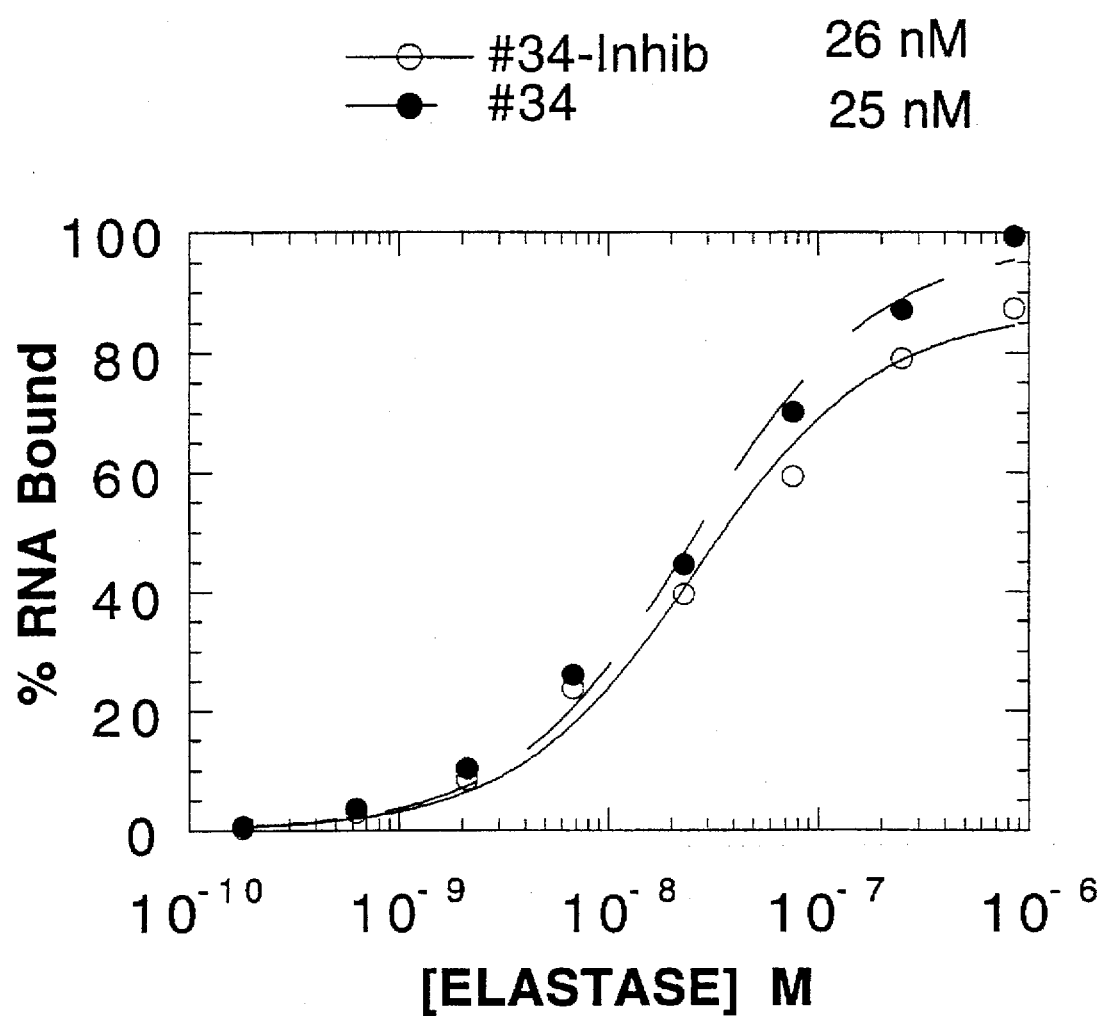
FIG. 4 shows the binding of representative ligand 34 (SEQ ID NO: 7) to elastase irreversibly bound to N-methoxysuccinyl-Ala-Ala-Pro-Val-chloromethyl ketone (o) (Kd=26 nM) or to native elastase (●)(Kd=25 nM).

Experiments were conducted to determine whether ligands bound the active site or the substrate binding site of elastase. The binding of ligand 34 to elastase irreversibly complexed with N-methoxysuccinyl-Ala-Ala-Pro-Val-chloromethyl ketone was studied. The chloromethyl ketone portion of the inhibitor irreversibly binds at the active site of elastase, with the tetrapeptide portion occupying the substrate binding pocket (Navia et al. (1989) Proc. Natl. Aced. Sci. USA 86:7). The results, shown in FIG. 4, show that ligand 34 bound to complexed elastase to the same extent as to the native enzyme. These results support the conclusion that the ligands do not bind at the active site or the substrate binding pocket of elastase. Ligand-mediated elastase inhibition may come from either ligand binding near the active site or to a remote site of the enzyme surface, inducing an allosteric change in the enzyme which impairs catalytic activity to some extent.

Figure 5:
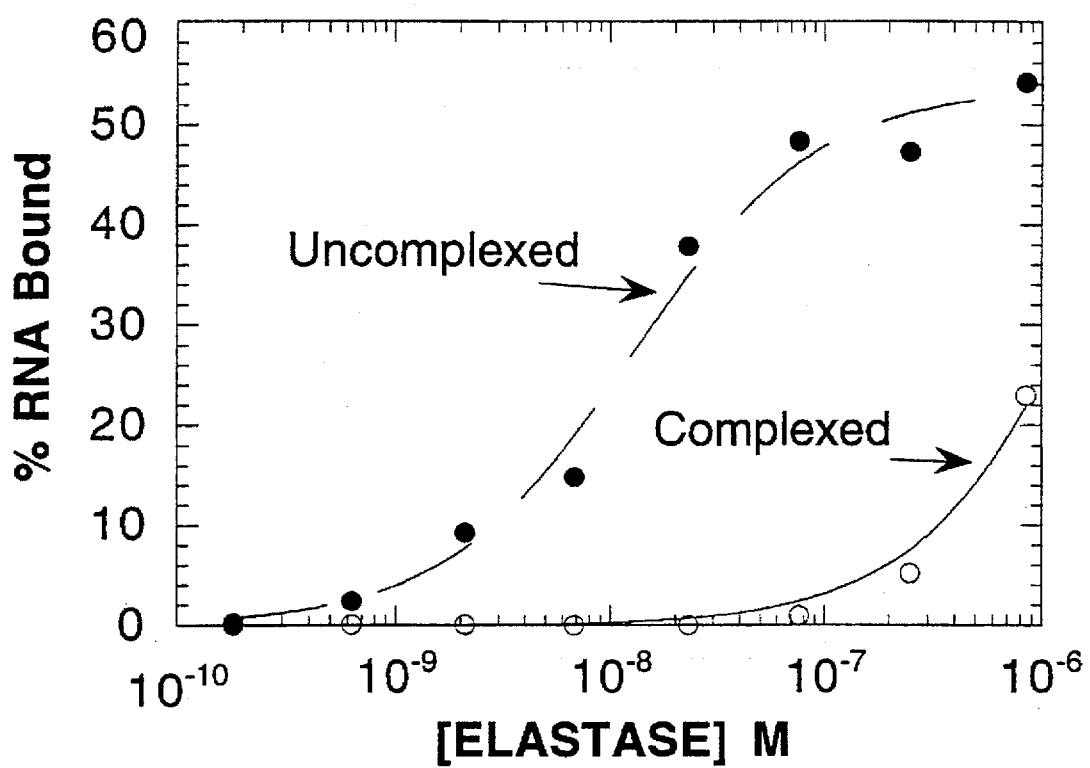
FIG. 5 shows the binding of representative ligand 34 (SEQ ID NO:7) to elastase complexed with α-1-proteinase inhibitor (α-1PI) (o) or native elastase (●)

A natural inhibitor for elastase, α-1-antitrypsin (α-1PI), forms a tight irreversible enzyme-inhibitor complex with elastase. The binding of ligand 34 to α-1PI-complexed elastase was examined. The results show (FIG. 5) that ligand 34 did not bind the complexed enzyme. One possible explanation for the lack of binding is that the ligand binds to a site on the face of elastase that interacts with α-1PI. Alternatively, α-1PI binding may induce a conformation change in elastase that abolishes ligand binding.

Figure 6:
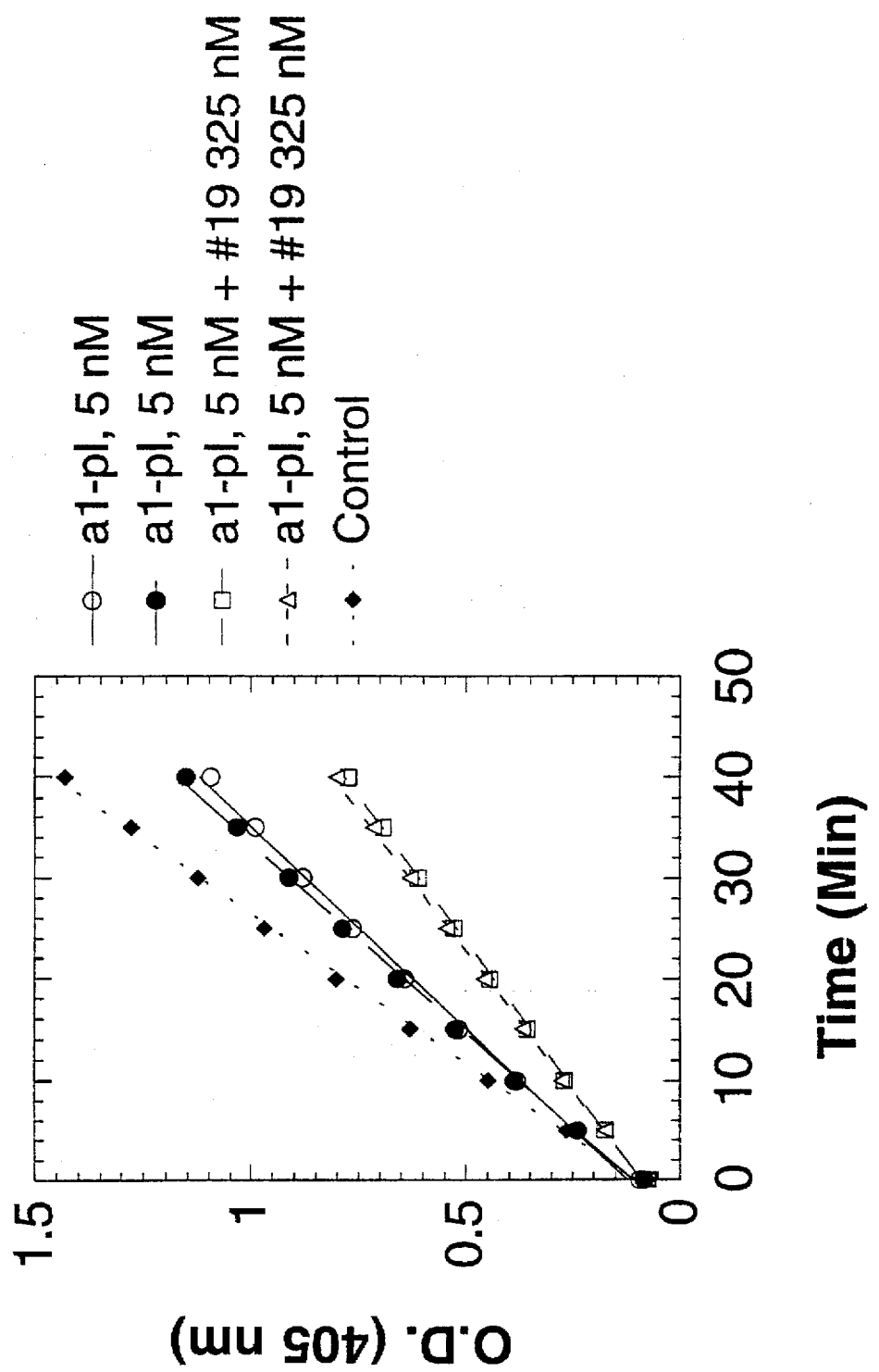
FIG. 6 shows the additive effect of representative ligand 19 (SEQ ID NO:15) on α-1PI-induced inhibition of elastase. Generation of p-nitroanilide was measured in the presence of elastase alone (♦), 5 nM α-1PI (o and ●), 5 nM α-1PI and 325 nM ligand 19 (□ and Δ).

The effect of ligand binding on α-1PI-induced inhibition was examined. Representative ligand 19 was found to act additively with α-1PI inhibition, enhancing the inhibitory activity of the natural inhibitor (FIG. 6).

Figure 7:
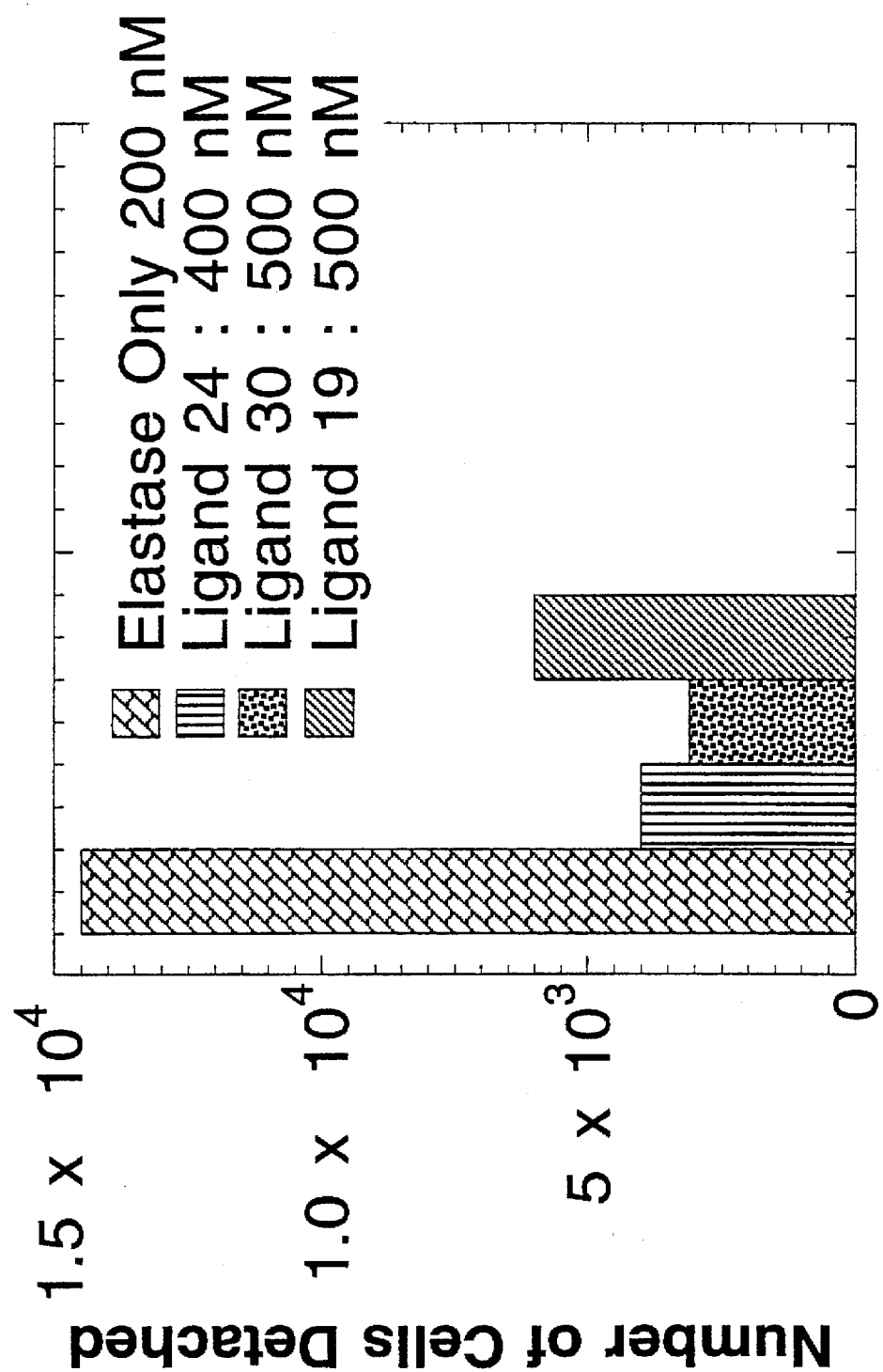
FIG. 7 shows the results of a cell detachment assay conducted with elastase only, or elastase in the presence of an inhibitory ligand (24 (SEQ ID NO:8), 30 (SEQ ID NO:1) or 19 (SEQ ID NO:15)).

A cell detachment assay was conducted with inhibitory ligands 24, 30, and 19. As shown in FIG. 7, all of the ligands substantially inhibited elastase activity.

EXAMPLE 4

Truncated Elastase Ligands

With the use of PCR primers specific for the 3' sequence of the 2'-NH$_2$ modified RNA ligand, the 3'-fixed regions for four different ligands (class I ligand 12, class II ligand 14, class III ligand 9 and class IV ligand 19) were eliminated. The results (Table 4) indicate that the 3'-fixed region is not necessary for high affinity binding for ligands 12 (class I) and 14 (class II). Both 3'-truncated ligands (64 nucleotides) had Kds similar to those of the full length ligands (87 nucleotides). However, the removal of the 3'-fixed region was deleterious for ligands 19 and 9. The 3'-fixed end, therefore, appears to be critical for enzyme inhibition by these ligands.

EXAMPLE 5

Effect of Monovalent Cations on Secondary Structure Formation

Figure 8B:
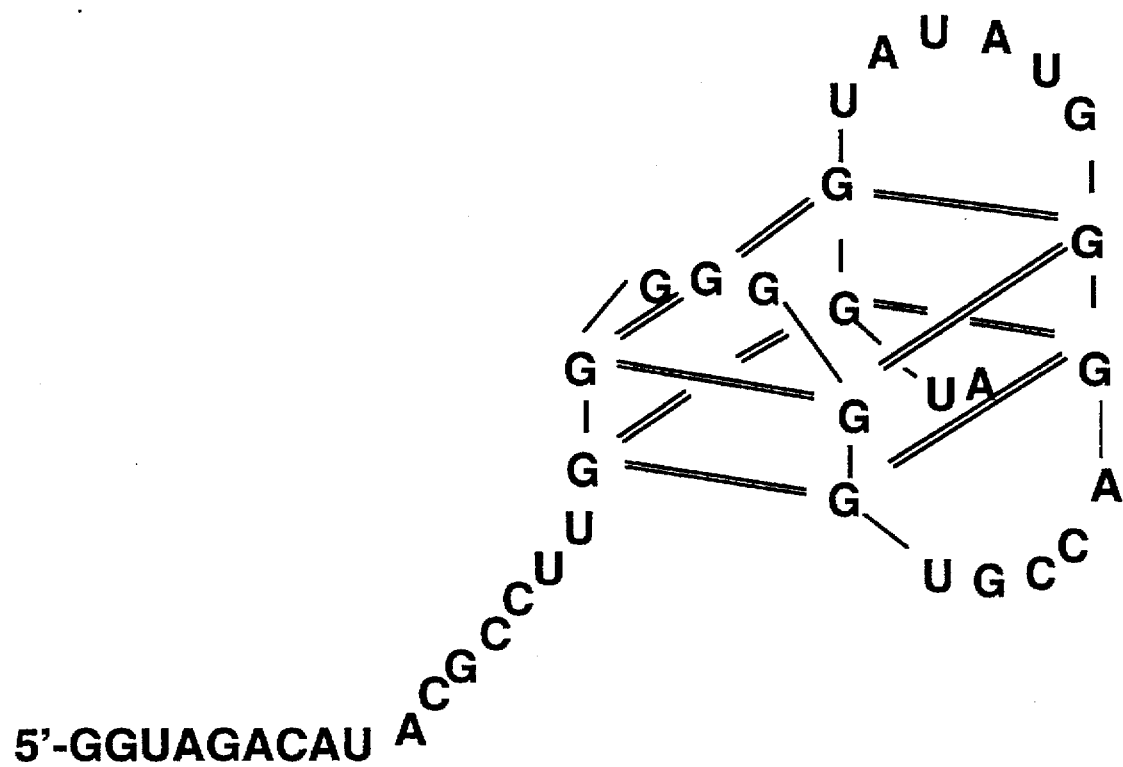

The three-dimensional molecular structure(s) assumed by the 2'-NH$_2$ modified elastase ligands of the present invention in the binding buffer is not known with certainty. However, the following evidence suggests these ligands form G-quartet structures (FIG. 8). It has been proposed that 2'-NH$_2$-substituted RNA has an unusually low melting temperature in helix-coil transition compared to that of 2'-OH RNA analogs. If so, this would argue against the formation of stem-loop structures in class I and II ligands. It is possible that SELEX with 2'-NH$_2$ ligands is inherently resistant to the production of RNA ligands with helical structures. This prediction remains to be tested.

Figure 9A:
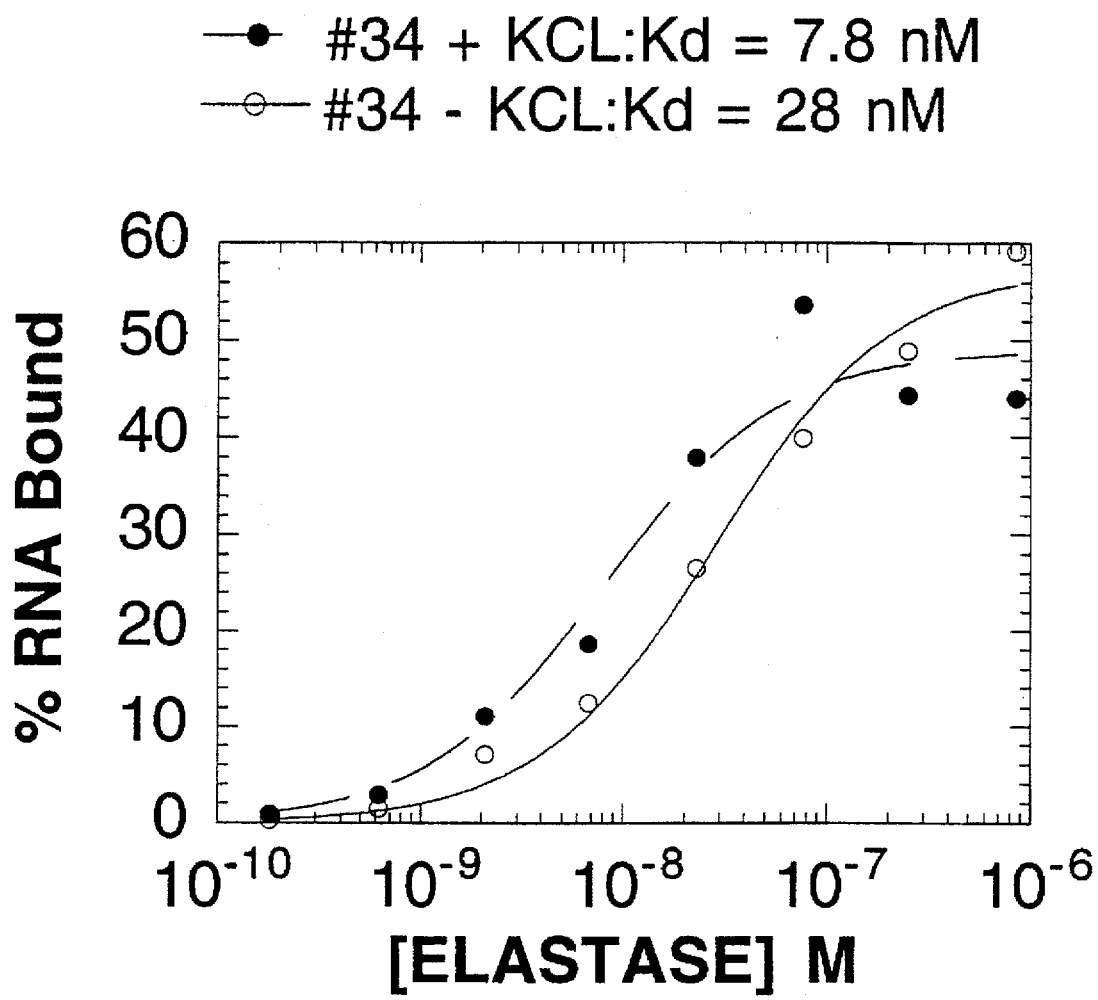
FIGS. 9A, 9B and 9C show the binding affinities of ligands 21 (SEQ ID NO:5), 24 (SEQ ID NO:8), and 34 (SEQ ID NO:7), respectively, to elastase in the presence and absence of 6 mM KCl.
Figure 9B:
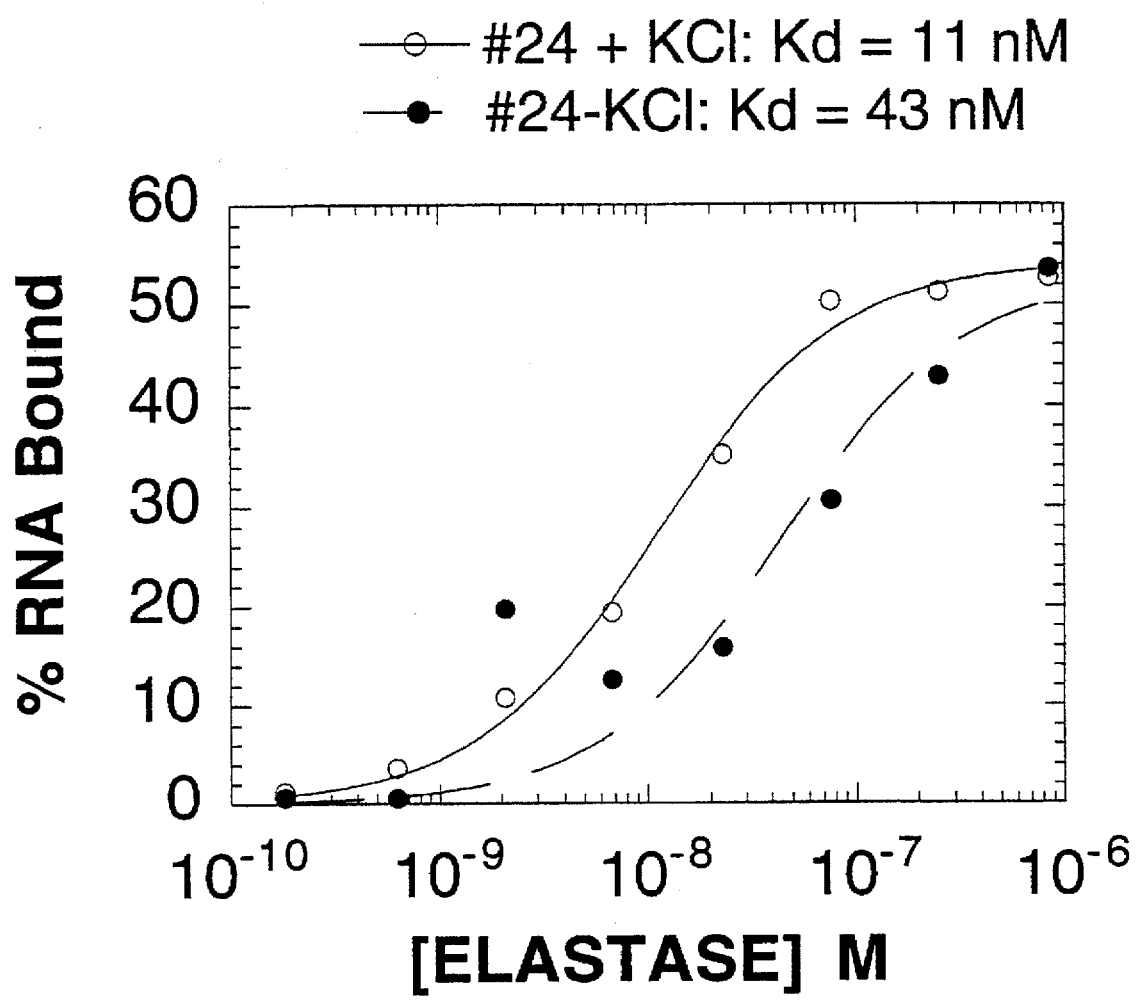
Figure 9C:
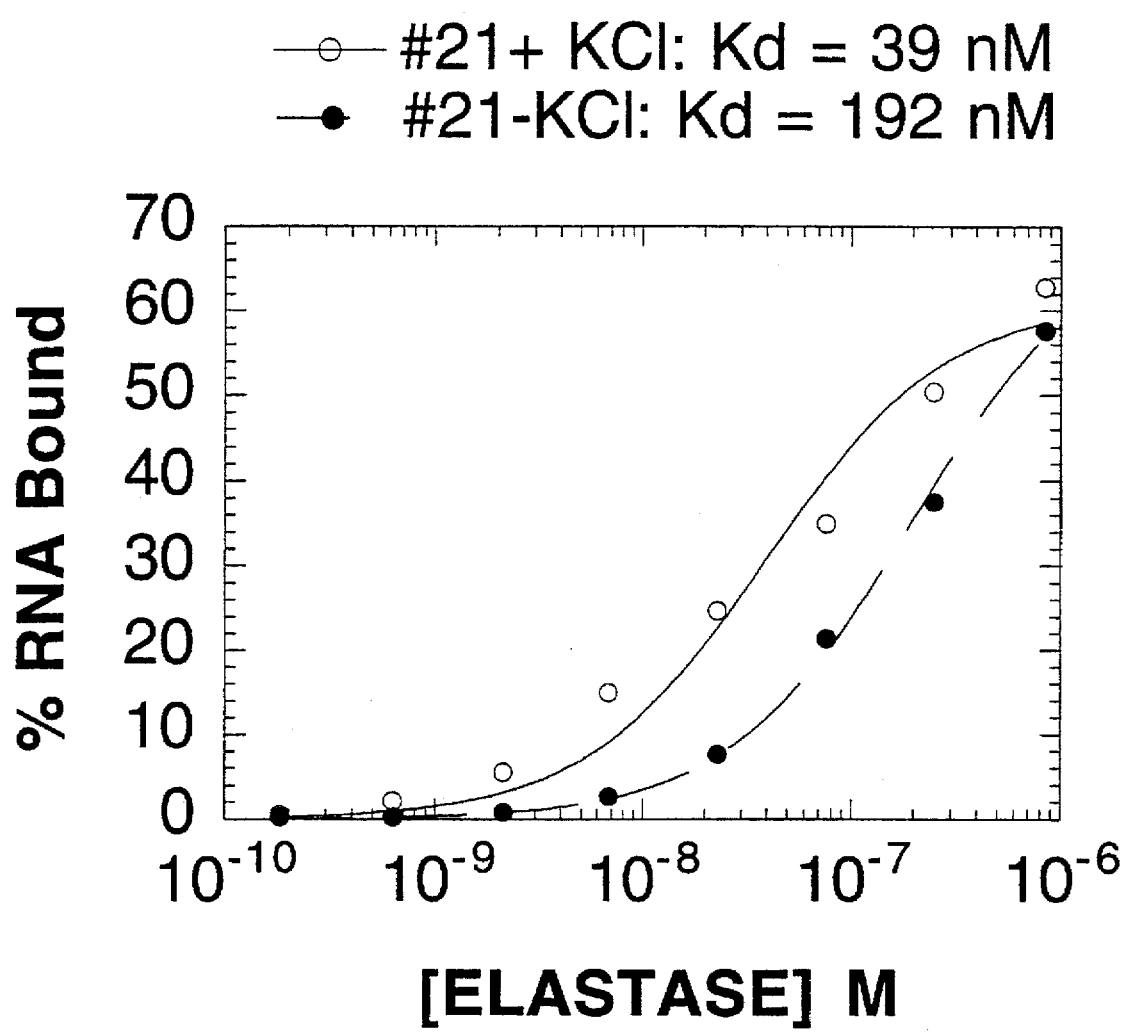

The binding buffer employed with 2'-NH$_2$ SELEX contained 6 mM KCl, a monovalent ion known to stabilize the G-quartet structure. The absence of KCl in the binding buffer affects the binding affinity of three clones (21, 24 and 34). As shown in FIG. 9, there was a significant change in Kd values in the presence and absence of KCl. For example, clone 21 had a Kd for elastase of 39 nM, in the presence of KCl, which dropped to 192 nM in the absence of KCl. This suggests that KCl has an important role in ligand binding, perhaps by favoring the formation of secondary structures with high binding affinity to elastase.

Ligand binding to elastase was then investigated with ligands 30 (class I), 34 (class II), and 9 (class III) in a binding buffer (150 mM XCl, 100 mM Tris-HCL (pH 7.0), 2 mM MgCl$_2$) where X is Li, K, or Tris (Table 5). The purpose of this experiment was to compare affinity in the presence of K (which favors formation of the G-quartet structure), Li (which does not favor formation of the G-quartet structure), or Tris (which does not affect formation of the G-quartet structure). The affinities of ligands belonging to classes I and II were higher in 150 mM than in 6 mM KCl buffer. This suggests that the fraction of high affinity secondary structures can be increased by increasing KCl concentration. However, ligand 9 (class III) had lower elastase affinity in the presence of high KCl, suggesting that the secondary structure of ligand 9 may be different from that assumed by class I and II ligands. The lowest affinity of class I and II ligands to elastase was seen in the presence of Li, the monovalent cation that does not favor formation of G-quartet structures.

In the presence of Tris buffer, all three ligands exhibited a moderately high affinity for elastase (however, lower than that of class I and II ligands in KCl buffer). A possible contamination of the Tris with $K^+$ may be responsible, or alternatively, $Mg^{++}$ ions may be involved in establishment of secondary structures in the absence of a high concentration of a monovalent ion. Some evidence for the stabilization of RNA G-quartet structures by $M^{++}$ has been published (Sundquist and Heaphy (1993) Proc. Natl. Acad. Sci. USA 90:3393).

EXAMPLE 6

Effect of pH on 2'-NH₂RNA and Non-Modified Single-Stranded DNA Ligand Binding to Elastase The pKa of 2'-NH₂-NTPs (nucleotide triphosphates) is approximately 6.5, not distant from the physiological pH range of 7.35–7.45. Therefore, at a physiological pH, a given RNA molecule containing 2'-NH₂-modified NTPs should have a distribution of protonated and unprotonated 2'-NH₂ groups. Consequently, it is likely that a small change in pH can affect the degree of protonation of a ligand, which may affect its binding to a target molecule.

Figure 10:
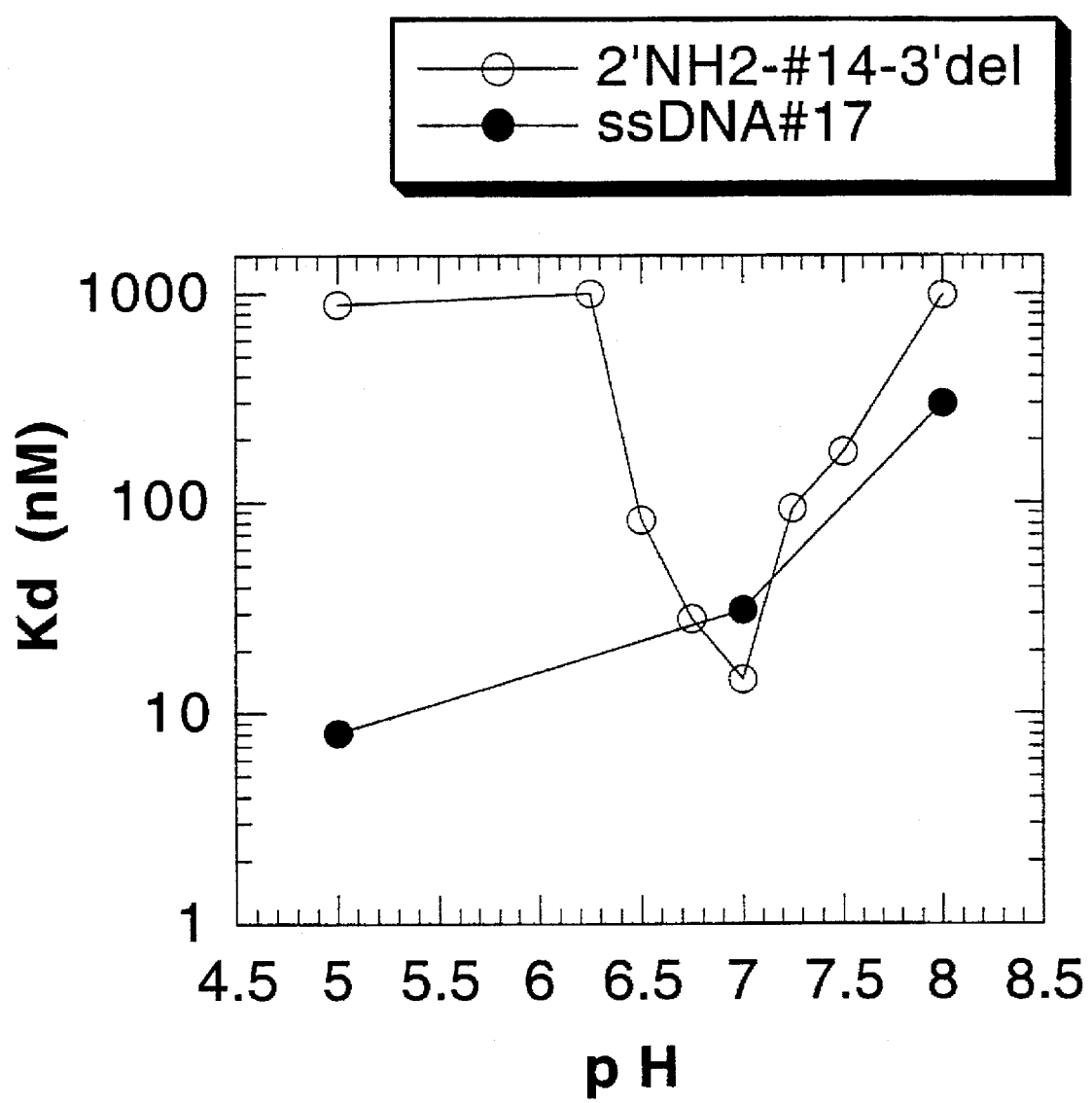
FIG. 10 show the effect of pH on binding of 2'-$NH_2$ RNA ligand 14 (SEQ ID NO:10) (3'-fixed sequence truncate) and non-modified single-stranded DNA ligand 17 (SEQ ID NO:1) to elastase.

The binding to elastase of representative 2'-NH₂ RNA ligand 14 and non-modified single-stranded DNA ligand 17 was examined over a pH range of 5.0–8.0. The results are shown in FIG. 10. The binding of the 2'-NH₂ RNA ligand was profoundly affected by pH. For example, the Kd increased more than 10-fold from pH 6.5 to pH 6.25. The optimum binding for the 2'-NH₂ ligand is seen at pH 7.0 the pH at which SELEX was conducted. The ssDNA ligand bound better at pH 5 and the Kd increased approximately 3 fold over two pH units.

EXAMPLE 7

Nucleic Acid Mimetics

The connecting loop nucleotides of the G-quartet structure was replaced with a synthetic linker tether group (FIG. 11). DNA-17 (TAGCGATACTGCGTGGGTTGGGGCGGGT AGGGCCAGCAGTCTCGTGCGGTACTTGAGCA) (SEQ ID NO:52) was synthesized with two loop nucleotides replaced by a 18-carbon ethylene glycol linker (Spacer phosphoramidite; Clonetech) to obtain a mimetic sequence, 17-LQT (TAGCGAT ACTGCGTGGGLGGGLGGGLGGG CCAGCAGTCTCGTGCGGTACTTGAGCA) (SEQ ID NO:53). L stands for the ethylene glycol linker. The length of the internucleotide phosphate is about a 3-carbon distance. Thus, the 18-carbon linker was expected to have enough flexibility to loop back into a G-quartet. 17-LQT was found not to bind elastase with significant affinity, however.

The absence of high affinity binding could be due to lack of loop nucleotides that are crucial for protein recognition or due to the synthetic tether restricting the oligonucleotide to fold into a tetraplex.

TABLE 1

2'-NH₂ RNA LIGANDS TO ELASTASE.

| | | SEQ ID NO: |
|---|---|---|
| CLASS I | | |
| Clone 12, 13, 17, 20, 29, | GAGUAGGCUUGACGCCUGGGGGGGUAUGGCUUCGACUGCG | 1 |
| 30, 31, 33, 43, 55, 58 | ------------------------------A------ | 2 |
| Clone 42 | ---------------- ------------------U---- | 3 |
| Clone 44 | A---G---------------------------C-------- | 4 |
| Clone 16 | | |
| CLASS II | | |
| Clone 21, 56 | GGUAGACAUACGCCUUGGGGGGGUGUCAGGGUAUAUGGUA | 5 |
| Clone 57 | --C------------------------------------ | 6 |
| Clone 34 | -----------------------C--------------- | 7 |
| Clone 24 | -------------------------A------------- | 8 |
| Clone 2 | --C---------------------------------C- | 9 |
| Clone 14 | --C------------------U-------------C- | 10 |
| CLASS III | | |
| Clone 45, 10 | AGAAUGAAUGUGAUGAACAGGUGUCGGGGUGGAUGGGUGG | 11 |
| Clone 9 | G--------------------------------------- | 12 |
| Clone 6 | -AA------------------------------------- | 13 |
| Clone 26 | C-CC-U-G-CGCCAU--UGC--------------A----- | 14 |
| CLASS IV | | |
| Clone 8, 19, 41 | UGCCCGGCAGUACUGCACGGCCUCGGGGGGGACCAGGGAG | 15 |
| Clone 28 | AU-GGAUAGCGC-GCG-U---G--U---------------- | 16 |
| CLASS V | | |
| Clone 60 | GUACUACUGCAAGCCCGUGUGGCGCGGUCAGUGGGUGGC | 17 |
| Clone 35 | ----------------------------------------C | 18 |
| Clone 4 | CGGAUCGGGCGGUCGU-UA-C--GAU--CGU-C------A | 19 |
| Clone 50 | UGAC-GGG-CG-CAUG-C---A--U-U---C---------- | 20 |
| Clone 22 | GGCC--CUG-A--GUCUG----U---U----------··· | 21 |
| Clone 25 | UGACCGGG-C-AC-UG-UUGAG-UGUG-CC----------- | 22 |

TABLE 1-continued

2'-NH$_2$ RNA LIGANDS TO ELASTASE.

SEQ ID NO:

CLASS VI

| | | |
|---|---|---|
| Clone 11 | GACGCGUGCUGGCCUCGACCGUGUGGGUGCGGAUGGGUGG | 23 |
| Clone 3 | UGAG--UGA-UAG----UGGUAA---CCA----C-----G--GUCGG | 24 |
| Clone 46 | UG-AUA-CGCUG-GU-----C-CU--G-G--U----CA--G | 25 |

TABLE 2

Kds OF REPRESENTATIVE LIGANDS

| CLASS | CLONE NUMBER | SEQ ID NO. | Kd (ηM) |
|---|---|---|---|
| I | 30 | 1 | 10 |
|   | 44 | 3 | 28 |
| II | 21 | 5 | 39 |
|   | 14 | 10 | 17 |
|   | 24 | 8 | 11 |
|   | 34 | 7 | 8 |
| III | 9 | 12 | 10 |
|   | 26 | 14 | 38 |
| IV | 19 | 15 | 8 |
|   | 28 | 16 | 57 |
| V | 4 | 19 | 172 |
|   | 22 | 21 | 24 |
| VI | 3 | 24 | 28 |
|   | 46 | 25 | 13 |

TABLE 3

SPECIFICITY OF 2'-NH$_2$ LIGANDS TO ELASTASE

| LIGAND | SEQ ID NO. | ELASTASE | Kd for THROMBIN | Kd for bFGF |
|---|---|---|---|---|
| Class II clone 24 | 8 | 11 ηM | 0.6 μM | >1 μM |
| Class III, clone 9 | 12 | 9.7 ηM | — | 0.5 μM |

TABLE 4

BINDING OF TRUNCATED 2'-NH$_2$ LIGANDS TO ELASTASE

| | | | Kd (ηM) | |
|---|---|---|---|---|
| CLASS | LIGAND | SEQ ID NO. | Full Length | 3'-Truncated |
| I | 12 | 1 | 10 | 10 |
| II | 14 | 10 | 17 | 14.5 |
| III | 9 | 12 | 10 | 989 |
| IV | 19 | 15 | 8 | 648 |

TABLE 5

THE EFFECT OF K$^+$, Li$^+$, AND TRIS ON BINDING OF 2'-NH$_2$ LIGANDS TO ELASTASE.

| | | | Kd (ηM) | | |
|---|---|---|---|---|---|
| CLASS | LIGAND | SEQ ID NO. | KCl | LiCl | Tris-HCl |
| I | 30 | 1 | 3.8 | 581 | 38 |
| II | 34 | 7 | 5.5 | 669 | 59 |
| III | 9 | 12 | 378 | 231 | 34 |

TABLE 6

SINGLE-STRANDED DNA LIGANDS TO ELASTASE.

| CLONE | SEQUENCE | SEQ ID NO: |
|---|---|---|
| 1 | ACCTTTTCCTCTCAGTCTTCTTATCTCGCCTATTATTATT | 26 |
| 2 | GCGTGGGTTGGGGCCGGGAGGGCCAGCAGTCTCGTGCGTC | 27 |
| 3 | CATTCATCTTCTCATTCTCGCCTAACTGTACACATCTTT | 28 |
| 4 | GCGTGGGTTGGGGCCGGGAGGGCCAGCAGTCTCGTGCGT | 29 |
| 5 | GCGTGGGTTGGGGCCGGGAGGGCCAACAGTCTCGTGCGTC | 30 |
| 6 | CTACCCTTTCTTGACCACCGCCTCGTTTCATCCACCTTAC | 31 |
| 7 | TTCTTTCTATACCCATATTACCCTTCTTCACACTCGTATC | 32 |
| 14 | CTTTATCCTTTCTCTTTCCTTGCACTCTAACATCCTACTC | 33 |
| 15 | GCGTGGGTTGGGGCCGGTAGGGCCAGCAGTCTCGTTGCGT | 34 |
| 16 | CCTTCTTGTTATATTGGTCGTTTTCTTCTTTTACTTTCTT | 35 |
| 17 | TCTTCATCATTTCACTTCATTCTGTCGGGCTATCTTCGGT | 36 |
| 18 | TTCCACGTCTCCTCAGCCCGGGAGGCCACCTTTTTATCTG | 37 |

TABLE 6-continued

SINGLE-STRANDED DNA LIGANDS TO ELASTASE.

| CLONE | SEQUENCE | SEQ ID NO: |
|---|---|---|
| 19 | GAAGGCTTAACCTAATTTTCCACCTTTCATCCACTTTTCC | 38 |
| 20 | TCACCTCCCATTTATATTTTCCCTTAATTTCTTCTTCTTA | 39 |
| 23 | CTTACTATGCATCTTACTTATTATTTTTTTTTACTTTCTA | 40 |
| 24 | TACTTCTTTTACATCATTCCTCGATTTATTCATTCTCCAC | 41 |
| 25 | TTCACCCGTGTCATATCATATTTCCCGGTCCTTCCTTTCCC | 42 |
| 28 | CAATTCAAACCTTTTCTACAATTTTCATCTTACATTCTTC | 43 |
| 44 | TCACTTGATCCTTCTTTACTTTTTTTCTCGTCTAATTATA | 44 |
| 45 | GCGTGGGTTGGGGCGGGATGGGCCAGCAGTCTCGTGCGGT | 45 |
| 46 | CTTTTTATTCCAACCCCCATTCTTACTTACAATATCTTGA | 46 |
| 47 | TATCCTTCTCCTTAACTCCTACTTCTATCTATAAAATTAT | 47 |
| 11 | GCGTGGGTAGGGGCCGGGAGGGCCAGCAGTCACGTGCGTA | 48 |
| 50 | GGGTGGGTTGGGGCCGGGAGGGCTAGCAGTCTCGTGCGTT | 49 |
| 51 | GCGTGGGATGGGGCCGGGAGGGCCAGCAGTCTCGTGCGTT | 50 |
| 58 | GCGTGGGTTGGGGCCGGGAGGGCCAGCAGTCTCGTGCGT | 51 |

---

We claim:

1. A nucleic acid ligand to elastase identified according to a method comprising the steps of:
   a) contacting a candidate mixture of nucleic acids with elastase, wherein nucleic acids having an increased affinity to elastase relative to the candidate mixture may be partitioned from the remainder of the candidate mixture;
   b) partitioning the increased affinity nucleic acids from the remainder of the candidate mixture; and
   c) amplifying the increased affinity nucleic acids to yield a ligand-enriched mixture of nucleic acids, whereby a nucleic acid ligand to elastase may be identified.

2. A purified and isolated non-naturally occurring RNA ligand to elastase.

3. The RNA ligand of claim 2 wherein said ligand is selected from the group consisting of the sequences set forth in Table 1.

4. The RNA ligand of claim 2 wherein said ligand is comprised of 2'-amino (2'-NH$_2$) modified nucleotides.

5. A purified and isolated non-naturally occurring DNA ligand to elastase.

6. The DNA ligand of claim 5 wherein said ligand is selected from the group consisting of the sequences set forth in Table 6.

7. A purified and isolated non-naturally occurring nucleic acid ligand to elastase identified according to a method comprising the steps of:
   a) contacting a candidate mixture of nucleic acids with elastase, wherein nucleic acids having an increased affinity to elastase relative to the candidate mixture may be partitioned from the remainder of the candidate mixture;
   b) partitioning the increased affinity nucleic acids from the remainder of the candidate mixture; and
   c) amplifying the increased affinity nucleic acid to yield a ligand enriched mixture of nucleic acids, whereby a nucleic acid ligand to elastase may be identified.

8. The nucleic acid ligand of claim 1 which is a ribonucleic acid ligand.

9. The RNA ligand of claim 8 wherein said ligand is selected from the group consisting of the sequences set forth in Table 1.

10. The RNA ligand of claim 8 wherein said ligand is comprised of 2'-amino (2'-NH$_2$) modified nucleotides.

11. The nucleic acid ligand of claim 1 which is a deoxyribonucleic acid ligand.

12. The DNA ligand of claim 11 wherein said ligand is selected from the group consisting of the sequences set forth in Table 6.

* * * * *